US009615780B2

(12) United States Patent
Hayter

(10) Patent No.: US 9,615,780 B2
(45) Date of Patent: Apr. 11, 2017

(54) METHOD AND APPARATUS FOR PROVIDING DATA PROCESSING AND CONTROL IN MEDICAL COMMUNICATION SYSTEM

(75) Inventor: Gary Hayter, Oakland, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 1394 days.

(21) Appl. No.: 12/102,847

(22) Filed: Apr. 14, 2008

(65) Prior Publication Data

US 2008/0256048 A1 Oct. 16, 2008

Related U.S. Application Data

(60) Provisional application No. 60/911,872, filed on Apr. 14, 2007.

(51) Int. Cl.
| | |
|---|---|
| *A61B 5/05* | (2006.01) |
| *C12Q 1/54* | (2006.01) |
| *A61B 5/145* | (2006.01) |
| *A61B 5/1486* | (2006.01) |
| *A61B 5/1495* | (2006.01) |
| *A61B 5/00* | (2006.01) |

(52) U.S. Cl.
CPC .......... *A61B 5/14532* (2013.01); *A61B 5/002* (2013.01); *A61B 5/1495* (2013.01); *A61B 5/14865* (2013.01); *A61B 5/6867* (2013.01); *A61B 5/74* (2013.01); *A61B 5/742* (2013.01); *A61B 5/7405* (2013.01); *A61B 5/746* (2013.01); *A61B 2560/0252* (2013.01); *A61B 2560/0271* (2013.01); *C12Q 1/54* (2013.01)

(58) Field of Classification Search
None
See application file for complete search history.

(56) References Cited

U.S. PATENT DOCUMENTS

| | | |
|---|---|---|
| 3,581,062 A | 5/1971 | Aston |
| 3,926,760 A | 12/1975 | Allen et al. |
| 3,949,388 A | 4/1976 | Fuller |
| 3,960,497 A | 6/1976 | Acord et al. |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,431,004 A | 2/1984 | Bessman et al. |
| 4,441,968 A | 4/1984 | Emmer et al. |
| 4,464,170 A | 8/1984 | Clemens et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,847,785 A | 7/1989 | Stephens |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,051,688 A | 9/1991 | Murase et al. |
| 5,055,171 A | 10/1991 | Peck |
| 5,068,536 A | 11/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,135,004 A | 8/1992 | Adams et al. |
| 5,165,407 A | 11/1992 | Wilson et al. |
| 5,202,261 A | 4/1993 | Musho et al. |

(Continued)

FOREIGN PATENT DOCUMENTS

| | | |
|---|---|---|
| CA | 2143172 | 7/2005 |
| CA | 2396613 | 3/2008 |

(Continued)

OTHER PUBLICATIONS

Aussedat et al. A user-friendly method for calibrating a subcutaneous glucose sensor-based hypoclycaemic alarm Biosensors and Bioelectronics vol. 12, pp. 1061-1071 (1997).*

(Continued)

*Primary Examiner* — John S Brusca
(74) *Attorney, Agent, or Firm* — One LLP

(57) ABSTRACT

Methods and apparatus for providing data processing and control for use in a medical communication system are provided.

27 Claims, 10 Drawing Sheets

(56) References Cited

U.S. PATENT DOCUMENTS

| | | |
|---|---|---|
| 5,204,264 A | 4/1993 | Kaminer et al. |
| 5,210,778 A | 5/1993 | Massart |
| 5,228,449 A | 7/1993 | Christ et al. |
| 5,231,988 A | 8/1993 | Wernicke et al. |
| 5,246,867 A | 9/1993 | Lakowicz et al. |
| 5,251,126 A | 10/1993 | Kahn et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,408,999 A | 4/1995 | Singh et al. |
| 5,410,326 A | 4/1995 | Goldstein |
| 5,411,647 A | 5/1995 | Johnson et al. |
| 5,425,868 A | 6/1995 | Pedersen |
| 5,429,602 A | 7/1995 | Hauser |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,532,686 A | 7/1996 | Urbas et al. |
| 5,552,997 A | 9/1996 | Massart |
| 5,564,434 A * | 10/1996 | Halperin et al. ............... 600/488 |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,634,468 A | 6/1997 | Platt et al. |
| 5,653,239 A | 8/1997 | Pompei et al. |
| 5,660,163 A | 8/1997 | Schulman et al. |
| 5,665,222 A | 9/1997 | Heller et al. |
| 5,707,502 A | 1/1998 | McCaffrey et al. |
| 5,711,001 A | 1/1998 | Bussan et al. |
| 5,711,861 A | 1/1998 | Ward et al. |
| 5,724,030 A | 3/1998 | Urbas et al. |
| 5,726,646 A | 3/1998 | Bane et al. |
| 5,733,259 A | 3/1998 | Valcke et al. |
| 5,735,285 A | 4/1998 | Albert et al. |
| 5,748,103 A | 5/1998 | Flach et al. |
| 5,749,907 A | 5/1998 | Mann |
| 5,772,586 A | 6/1998 | Heinonen et al. |
| 5,791,344 A | 8/1998 | Schulman et al. |
| 5,804,047 A | 9/1998 | Karube et al. |
| 5,833,603 A | 11/1998 | Kovacs et al. |
| 5,842,189 A | 11/1998 | Keeler et al. |
| 5,891,049 A | 4/1999 | Cyrus et al. |
| 5,899,855 A | 5/1999 | Brown |
| 5,914,026 A | 6/1999 | Blubaugh, Jr. et al. |
| 5,925,021 A | 7/1999 | Castellano et al. |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,980,708 A | 11/1999 | Champagne et al. |
| 5,995,860 A | 11/1999 | Sun et al. |
| 6,001,067 A | 12/1999 | Shults et al. |
| 6,024,699 A | 2/2000 | Surwit et al. |
| 6,028,413 A | 2/2000 | Brockmann |
| 6,049,727 A | 4/2000 | Crothall |
| 6,052,565 A | 4/2000 | Ishikura et al. |
| 6,066,243 A | 5/2000 | Anderson et al. |
| 6,083,710 A | 7/2000 | Heller et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,096,364 A | 8/2000 | Bok et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,130,623 A | 10/2000 | MacLellan et al. |
| 6,134,461 A | 10/2000 | Say et al. |
| 6,143,164 A | 11/2000 | Heller et al. |
| 6,144,871 A | 11/2000 | Saito et al. |
| 6,159,147 A | 12/2000 | Lichter et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,233,471 B1 | 5/2001 | Berner et al. |
| 6,248,067 B1 | 6/2001 | Causey, III et al. |
| 6,254,586 B1 | 7/2001 | Mann et al. |
| 6,270,455 B1 | 8/2001 | Brown |
| 6,275,717 B1 | 8/2001 | Gross et al. |
| 6,283,761 B1 | 9/2001 | Joao |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,299,347 B1 | 10/2001 | Pompei |
| 6,306,104 B1 | 10/2001 | Cunningham et al. |
| 6,309,884 B1 | 10/2001 | Cooper et al. |
| 6,314,317 B1 | 11/2001 | Willis |
| 6,329,161 B1 | 12/2001 | Heller et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,471,689 B1 | 10/2002 | Joseph et al. |
| 6,478,736 B1 | 11/2002 | Mault |
| 6,484,046 B1 | 11/2002 | Say et al. |
| 6,493,069 B1 | 12/2002 | Nagashimada et al. |
| 6,496,729 B2 | 12/2002 | Thompson |
| 6,497,655 B1 | 12/2002 | Linberg et al. |

(56) References Cited

U.S. PATENT DOCUMENTS

| | | |
|---|---|---|
| 6,498,043 B1 | 12/2002 | Schulman et al. |
| 6,514,718 B2 | 2/2003 | Heller et al. |
| 6,520,326 B2 | 2/2003 | McIvor et al. |
| 6,544,212 B2 | 4/2003 | Galley et al. |
| 6,546,268 B1 | 4/2003 | Ishikawa et al. |
| 6,549,796 B2 | 4/2003 | Sohrab |
| 6,551,494 B1 | 4/2003 | Feldman et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,545 B2 | 6/2003 | Knobbe et al. |
| 6,574,490 B2 | 6/2003 | Abbink et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,648,821 B2 | 11/2003 | Lebel et al. |
| 6,654,625 B1 | 11/2003 | Say et al. |
| 6,656,114 B1 | 12/2003 | Poulsen et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,731,976 B2 | 5/2004 | Penn et al. |
| 6,733,446 B2 | 5/2004 | Lebel et al. |
| 6,735,183 B2 | 5/2004 | O'Toole et al. |
| 6,740,075 B2 | 5/2004 | Lebel et al. |
| 6,740,518 B1 | 5/2004 | Duong et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,789,195 B1 | 9/2004 | Prihoda et al. |
| 6,790,178 B1 | 9/2004 | Mault et al. |
| 6,804,558 B2 | 10/2004 | Haller et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,923,764 B2 | 8/2005 | Aceti et al. |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,983,176 B2 | 1/2006 | Gardner et al. |
| 6,990,366 B2 | 1/2006 | Say et al. |
| 6,997,907 B2 | 2/2006 | Safabash et al. |
| 6,998,247 B2 | 2/2006 | Monfre et al. |
| 6,999,854 B2 | 2/2006 | Roth |
| 7,003,336 B2 | 2/2006 | Holker et al. |
| 7,003,340 B2 | 2/2006 | Say et al. |
| 7,003,341 B2 | 2/2006 | Say et al. |
| 7,009,511 B2 | 3/2006 | Mazar et al. |
| 7,015,817 B2 | 3/2006 | Copley et al. |
| 7,016,713 B2 | 3/2006 | Gardner et al. |
| 7,020,508 B2 | 3/2006 | Stivoric et al. |
| 7,022,072 B2 | 4/2006 | Fox et al. |
| 7,022,219 B2 | 4/2006 | Mansouri et al. |
| 7,024,236 B2 | 4/2006 | Ford et al. |
| 7,024,245 B2 | 4/2006 | Lebel et al. |
| 7,025,425 B2 | 4/2006 | Kovatchev et al. |
| 7,027,848 B2 | 4/2006 | Robinson et al. |
| 7,027,931 B1 | 4/2006 | Jones et al. |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,305 B2 | 5/2006 | KenKnight et al. |
| 7,046,153 B2 | 5/2006 | Oja et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,074,307 B2 | 7/2006 | Simpson et al. |
| 7,081,195 B2 | 7/2006 | Simpson et al. |
| 7,082,334 B2 | 7/2006 | Boute et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,125,382 B2 | 10/2006 | Zhou et al. |
| 7,134,999 B2 | 11/2006 | Brauker et al. |
| 7,136,689 B2 | 11/2006 | Shults et al. |
| 7,153,265 B2 | 12/2006 | Vachon |
| 7,155,290 B2 | 12/2006 | Von Arx et al. |
| 7,167,818 B2 | 1/2007 | Brown |
| 7,171,274 B2 | 1/2007 | Starkweather et al. |
| 7,179,226 B2 | 2/2007 | Crothall et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,207,974 B2 | 4/2007 | Safabash et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,228,182 B2 | 6/2007 | Healy et al. |
| 7,237,712 B2 | 7/2007 | DeRocco et al. |
| 7,258,673 B2 | 8/2007 | Racchini et al. |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,295,867 B2 | 11/2007 | Berner et al. |
| 7,299,082 B2 | 11/2007 | Feldman et al. |
| 7,310,544 B2 | 12/2007 | Brister et al. |

(56) References Cited

U.S. PATENT DOCUMENTS

| | | |
|---|---|---|
| 7,317,938 B2 | 1/2008 | Lorenz et al. |
| 7,318,816 B2 | 1/2008 | Bobroff et al. |
| 7,324,850 B2 | 1/2008 | Persen et al. |
| 7,335,294 B2 | 2/2008 | Heller et al. |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,384,397 B2 | 6/2008 | Zhang et al. |
| 7,387,010 B2 | 6/2008 | Sunshine et al. |
| 7,399,277 B2 | 7/2008 | Saidara et al. |
| 7,402,153 B2 | 7/2008 | Steil et al. |
| 7,404,796 B2 | 7/2008 | Ginsberg |
| 7,419,573 B2 | 9/2008 | Gundel |
| 7,424,318 B2 | 9/2008 | Brister et al. |
| 7,460,898 B2 | 12/2008 | Brister et al. |
| 7,467,003 B2 | 12/2008 | Brister et al. |
| 7,468,125 B2 * | 12/2008 | Kraft et al. ............... 205/792 |
| 7,471,972 B2 | 12/2008 | Rhodes et al. |
| 7,474,992 B2 | 1/2009 | Ariyur |
| 7,492,254 B2 | 2/2009 | Bandy et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,547,281 B2 | 6/2009 | Hayes et al. |
| 7,565,197 B2 | 7/2009 | Haubrich et al. |
| 7,569,030 B2 | 8/2009 | Lebel et al. |
| 7,574,266 B2 | 8/2009 | Dudding et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |
| 7,615,007 B2 | 11/2009 | Shults et al. |
| 7,618,369 B2 | 11/2009 | Hayter et al. |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,651,845 B2 | 1/2010 | Doyle, III et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,659,823 B1 | 2/2010 | Killian et al. |
| 7,668,596 B2 | 2/2010 | Von Arx et al. |
| 7,699,775 B2 | 4/2010 | Desai et al. |
| 7,699,964 B2 | 4/2010 | Feldman et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,736,310 B2 | 6/2010 | Taub et al. |
| 7,741,734 B2 | 6/2010 | Joannopoulos et al. |
| 7,766,829 B2 | 8/2010 | Sloan et al. |
| 7,768,386 B2 | 8/2010 | Hayter et al. |
| 7,768,387 B2 | 8/2010 | Fennell et al. |
| 7,771,352 B2 | 8/2010 | Shults et al. |
| 7,774,145 B2 | 8/2010 | Brauker et al. |
| 7,778,680 B2 | 8/2010 | Goode et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,811,231 B2 | 10/2010 | Jin et al. |
| 7,813,809 B2 | 10/2010 | Strother et al. |
| 7,826,981 B2 | 11/2010 | Goode, Jr. et al. |
| 7,831,310 B2 | 11/2010 | Lebel et al. |
| 7,860,574 B2 | 12/2010 | Von Arx et al. |
| 7,882,611 B2 | 2/2011 | Shah et al. |
| 7,889,069 B2 | 2/2011 | Fifolt et al. |
| 7,899,511 B2 | 3/2011 | Shults et al. |
| 7,899,545 B2 | 3/2011 | John |
| 7,905,833 B2 | 3/2011 | Brister et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,920,906 B2 | 4/2011 | Goode et al. |
| 7,928,850 B2 | 4/2011 | Hayter et al. |
| 7,938,797 B2 | 5/2011 | Estes |
| 7,941,200 B2 | 5/2011 | Weinert et al. |
| 7,946,985 B2 | 5/2011 | Mastrototaro et al. |
| 7,955,258 B2 | 6/2011 | Goscha et al. |
| 7,970,448 B2 | 6/2011 | Shults et al. |
| 7,972,296 B2 | 7/2011 | Braig et al. |
| 7,974,672 B2 | 7/2011 | Shults et al. |
| 7,976,466 B2 | 7/2011 | Ward et al. |
| 7,978,063 B2 | 7/2011 | Baldus et al. |
| 7,999,674 B2 | 8/2011 | Kamen |
| 8,010,174 B2 | 8/2011 | Goode et al. |
| 8,010,256 B2 | 8/2011 | Oowada |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,150,321 B2 | 4/2012 | Winter et al. |
| 8,150,516 B2 | 4/2012 | Levine et al. |
| 8,179,266 B2 | 5/2012 | Hermle |
| 8,192,394 B2 | 6/2012 | Estes et al. |
| 8,216,138 B1 | 7/2012 | McGarraugh et al. |
| 8,282,549 B2 | 10/2012 | Brauker et al. |
| 8,461,985 B2 | 6/2013 | Fennell et al. |
| 8,597,570 B2 | 12/2013 | Terashima et al. |
| 2001/0037366 A1 | 11/2001 | Webb et al. |
| 2002/0019022 A1 | 2/2002 | Dunn et al. |
| 2002/0042090 A1 | 4/2002 | Heller et al. |
| 2002/0054320 A1 | 5/2002 | Ogino |
| 2002/0068860 A1 | 6/2002 | Clark |
| 2002/0072784 A1 | 6/2002 | Sheppard et al. |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0128594 A1 | 9/2002 | Das et al. |
| 2002/0147135 A1 | 10/2002 | Schnell |
| 2002/0161288 A1 | 10/2002 | Shin et al. |
| 2002/0169635 A1 | 11/2002 | Shillingburg |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0032867 A1 | 2/2003 | Crothall et al. |
| 2003/0032874 A1 | 2/2003 | Rhodes et al. |

(56) References Cited

U.S. PATENT DOCUMENTS

| | | |
|---|---|---|
| 2003/0042137 A1 | 3/2003 | Mao et al. |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0100040 A1 | 5/2003 | Bonnecaze et al. |
| 2003/0100821 A1 | 5/2003 | Heller et al. |
| 2003/0114897 A1 | 6/2003 | Von Arx et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0147515 A1 | 8/2003 | Kai et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0024553 A1 | 2/2004 | Monfre et al. |
| 2004/0039298 A1 | 2/2004 | Abreu |
| 2004/0040840 A1 | 3/2004 | Mao et al. |
| 2004/0041749 A1 | 3/2004 | Dixon |
| 2004/0045879 A1 | 3/2004 | Shults et al. |
| 2004/0054263 A1 | 3/2004 | Moerman et al. |
| 2004/0063435 A1 | 4/2004 | Sakamoto et al. |
| 2004/0064068 A1 | 4/2004 | DeNuzzio et al. |
| 2004/0099529 A1 | 5/2004 | Mao et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0133390 A1 | 7/2004 | Osorio et al. |
| 2004/0135684 A1 | 7/2004 | Steinthal et al. |
| 2004/0138588 A1 | 7/2004 | Saikley et al. |
| 2004/0146909 A1 | 7/2004 | Duong et al. |
| 2004/0147872 A1 | 7/2004 | Thompson |
| 2004/0152622 A1 | 8/2004 | Keith et al. |
| 2004/0167464 A1 | 8/2004 | Ireland et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0219664 A1 | 11/2004 | Heller et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0267300 A1 | 12/2004 | Mace |
| 2005/0001024 A1 | 1/2005 | Kusaka et al. |
| 2005/0004439 A1 | 1/2005 | Shin et al. |
| 2005/0004494 A1 | 1/2005 | Perez et al. |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0070774 A1 | 3/2005 | Addison et al. |
| 2005/0070777 A1 | 3/2005 | Cho et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0096516 A1 | 5/2005 | Soykan et al. |
| 2005/0112169 A1 | 5/2005 | Brauker et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0137530 A1 | 6/2005 | Campbell et al. |
| 2005/0143635 A1 | 6/2005 | Kamath et al. |
| 2005/0154271 A1 | 7/2005 | Rasdal et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187442 A1 | 8/2005 | Cho et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0251033 A1 | 11/2005 | Scarantino et al. |
| 2005/0272985 A1 | 12/2005 | Kotulla et al. |
| 2005/0277164 A1 | 12/2005 | Drucker et al. |
| 2005/0277912 A1 | 12/2005 | John |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0058588 A1 | 3/2006 | Zdeblick |
| 2006/0079740 A1 | 4/2006 | Silver et al. |
| 2006/0091006 A1 | 5/2006 | Wang et al. |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0156796 A1 | 7/2006 | Burke et al. |
| 2006/0166629 A1 | 7/2006 | Reggiardo |

(56) References Cited

U.S. PATENT DOCUMENTS

| | | |
|---|---|---|
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189863 A1 | 8/2006 | Peyser et al. |
| 2006/0193375 A1 | 8/2006 | Lee et al. |
| 2006/0202805 A1 | 9/2006 | Schulman et al. |
| 2006/0211072 A1 | 9/2006 | Ryan et al. |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0229512 A1 | 10/2006 | Petisce et al. |
| 2006/0247508 A1 | 11/2006 | Fennell |
| 2006/0247710 A1 | 11/2006 | Goetz et al. |
| 2006/0247985 A1 | 11/2006 | Liamos et al. |
| 2006/0253296 A1 | 11/2006 | Liisberg et al. |
| 2006/0258929 A1 | 11/2006 | Goode et al. |
| 2006/0272652 A1 | 12/2006 | Stocker et al. |
| 2006/0281985 A1 | 12/2006 | Ward et al. |
| 2006/0287691 A1 | 12/2006 | Drew |
| 2006/0290496 A1 | 12/2006 | Peeters et al. |
| 2006/0293607 A1 | 12/2006 | Alt et al. |
| 2007/0010950 A1 | 1/2007 | Abensour et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0032706 A1 | 2/2007 | Kamath et al. |
| 2007/0032717 A1 | 2/2007 | Brister et al. |
| 2007/0033074 A1 | 2/2007 | Nitzan et al. |
| 2007/0038044 A1 | 2/2007 | Dobbles et al. |
| 2007/0055799 A1 | 3/2007 | Koehler et al. |
| 2007/0060803 A1 | 3/2007 | Liljeryd et al. |
| 2007/0060814 A1 | 3/2007 | Stafford |
| 2007/0060869 A1 | 3/2007 | Tolle et al. |
| 2007/0060979 A1 | 3/2007 | Strother et al. |
| 2007/0066873 A1 | 3/2007 | Kamath et al. |
| 2007/0066956 A1 | 3/2007 | Finkel |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0078818 A1 | 4/2007 | Zvitz et al. |
| 2007/0093786 A1 | 4/2007 | Goldsmith et al. |
| 2007/0094216 A1 | 4/2007 | Mathias et al. |
| 2007/0100222 A1 | 5/2007 | Mastrototaro et al. |
| 2007/0106135 A1 | 5/2007 | Sloan et al. |
| 2007/0118405 A1 | 5/2007 | Campbell et al. |
| 2007/0124002 A1 | 5/2007 | Estes et al. |
| 2007/0149875 A1 | 6/2007 | Ouyang et al. |
| 2007/0156033 A1 | 7/2007 | Causey, III et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0191701 A1 | 8/2007 | Feldman et al. |
| 2007/0191702 A1 | 8/2007 | Yodfat et al. |
| 2007/0203407 A1 | 8/2007 | Hoss et al. |
| 2007/0203966 A1 | 8/2007 | Brauker et al. |
| 2007/0208244 A1 | 9/2007 | Brauker et al. |
| 2007/0208246 A1 | 9/2007 | Brauker et al. |
| 2007/0213657 A1 | 9/2007 | Jennewine et al. |
| 2007/0228071 A1 | 10/2007 | Kamen et al. |
| 2007/0232878 A1 | 10/2007 | Kovatchev et al. |
| 2007/0232880 A1 | 10/2007 | Siddiqui et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0253021 A1 | 11/2007 | Mehta et al. |
| 2007/0255321 A1 | 11/2007 | Gerber et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0270672 A1 | 11/2007 | Hayter |
| 2007/0271285 A1 | 11/2007 | Eichorn et al. |
| 2007/0282299 A1 | 12/2007 | Hellwig |
| 2007/0285238 A1 | 12/2007 | Batra |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0017522 A1 | 1/2008 | Heller et al. |
| 2008/0018433 A1 | 1/2008 | Pitt-Pladdy |
| 2008/0021436 A1 | 1/2008 | Wolpert et al. |
| 2008/0021666 A1 | 1/2008 | Goode et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0058773 A1 | 3/2008 | John |
| 2008/0060955 A1 | 3/2008 | Goodnow |
| 2008/0061961 A1 | 3/2008 | John |
| 2008/0064937 A1 | 3/2008 | McGarraugh et al. |
| 2008/0064943 A1 | 3/2008 | Talbot et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0097289 A1 | 4/2008 | Steil et al. |
| 2008/0108942 A1 | 5/2008 | Brister et al. |
| 2008/0114228 A1 | 5/2008 | McCluskey et al. |
| 2008/0119705 A1 | 5/2008 | Patel et al. |
| 2008/0139910 A1 | 6/2008 | Mastrototaro et al. |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0177149 A1 | 7/2008 | Weinert et al. |
| 2008/0182537 A1 | 7/2008 | Manku et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208026 A1 | 8/2008 | Noujaim et al. |
| 2008/0208113 A1 | 8/2008 | Damiano et al. |
| 2008/0214900 A1 | 9/2008 | Fennell et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234663 A1 | 9/2008 | Yodfat et al. |
| 2008/0234943 A1 | 9/2008 | Ray et al. |
| 2008/0235469 A1 | 9/2008 | Drew |

(56) References Cited

U.S. PATENT DOCUMENTS

| | | |
|---|---|---|
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0262469 A1 | 10/2008 | Brister et al. |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319085 A1 | 12/2008 | Wright et al. |
| 2008/0319279 A1 | 12/2008 | Ramsay et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088614 A1 | 4/2009 | Taub et al. |
| 2009/0093687 A1 | 4/2009 | Telfort et al. |
| 2009/0099436 A1 | 4/2009 | Brister et al. |
| 2009/0105554 A1 | 4/2009 | Stahmann et al. |
| 2009/0105560 A1 | 4/2009 | Solomon |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0112478 A1 | 4/2009 | Mueller, Jr. et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0227855 A1 | 9/2009 | Hill et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0240440 A1 | 9/2009 | Shurabura et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorensen |
| 2009/0253973 A1 | 10/2009 | Bashan et al. |
| 2009/0267765 A1 | 10/2009 | Greene et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0292188 A1 | 11/2009 | Hoss et al. |
| 2009/0296742 A1 | 12/2009 | Sicurello et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |

(56) References Cited

U.S. PATENT DOCUMENTS

| | | |
|---|---|---|
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121169 A1 | 5/2010 | Petisce et al. |
| 2010/0141656 A1 | 6/2010 | Krieftewirth |
| 2010/0152554 A1 | 6/2010 | Steine et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0185175 A1 | 7/2010 | Kamen et al. |
| 2010/0190435 A1 | 7/2010 | Cook et al. |
| 2010/0191082 A1 | 7/2010 | Brister et al. |
| 2010/0191472 A1 | 7/2010 | Doniger et al. |
| 2010/0198142 A1 | 8/2010 | Sloan et al. |
| 2010/0213080 A1 | 8/2010 | Celentano et al. |
| 2010/0240975 A1 | 9/2010 | Goode et al. |
| 2010/0274111 A1 | 10/2010 | Say et al. |
| 2010/0312176 A1 | 12/2010 | Lauer et al. |
| 2010/0313105 A1 | 12/2010 | Nekoomaram et al. |
| 2011/0004276 A1 | 1/2011 | Blair et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0077490 A1 | 3/2011 | Simpson et al. |
| 2011/0148905 A1 | 6/2011 | Simmons et al. |
| 2011/0152637 A1 | 6/2011 | Kateraas et al. |
| 2011/0208027 A1 | 8/2011 | Wagner et al. |
| 2011/0257895 A1 | 10/2011 | Brauker et al. |
| 2011/0287528 A1 | 11/2011 | Fern et al. |
| 2011/0289497 A1 | 11/2011 | Kiaie et al. |
| 2011/0320130 A1 | 12/2011 | Valdes et al. |
| 2012/0078071 A1 | 3/2012 | Bohm et al. |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2013/0035575 A1 | 2/2013 | Mayou et al. |
| 2013/0235166 A1 | 9/2013 | Jones et al. |

FOREIGN PATENT DOCUMENTS

| | | |
|---|---|---|
| CA | 2413148 | 8/2010 |
| DE | 4401400 | 7/1995 |
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 0724859 | 8/1996 |
| EP | 0678308 | 5/2000 |
| EP | 1048264 | 11/2000 |
| EP | 1292218 | 3/2003 |
| EP | 1077634 | 7/2003 |
| EP | 1568309 | 8/2005 |
| EP | 1666091 | 6/2006 |
| EP | 1703697 | 9/2006 |
| EP | 1704893 | 9/2006 |
| EP | 1897487 | 11/2009 |
| EP | 1897492 | 11/2009 |
| EP | 2113864 | 11/2009 |
| EP | 1897488 | 12/2009 |
| EP | 1681992 | 4/2010 |
| EP | 1448489 | 8/2010 |
| EP | 1971396 | 8/2010 |
| EP | 2201969 | 3/2011 |
| EP | 2153382 | 2/2012 |
| GB | 2409951 | 7/2005 |
| WO | WO-93/06237 | 4/1993 |
| WO | WO-96/25089 | 8/1996 |
| WO | WO-96/35370 | 11/1996 |
| WO | WO-97/33513 | 9/1997 |
| WO | WO-98/35053 | 8/1998 |
| WO | WO-99/56613 | 11/1999 |
| WO | WO-00/49940 | 8/2000 |
| WO | WO-00/59370 | 10/2000 |
| WO | WO-00/74753 | 12/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/058537 | 8/2002 |
| WO | WO-03/076893 | 9/2003 |
| WO | WO-03/082091 | 10/2003 |
| WO | WO-03/085372 | 10/2003 |
| WO | WO-2004/047445 | 6/2004 |
| WO | WO-2004/061420 | 7/2004 |
| WO | WO-2005/010756 | 2/2005 |
| WO | WO-2005/040404 | 5/2005 |
| WO | WO-2005/041766 | 5/2005 |
| WO | WO-2005/045744 | 5/2005 |
| WO | WO-2005/089103 | 9/2005 |
| WO | WO-2005/119238 | 12/2005 |
| WO | WO-2006/024671 | 3/2006 |
| WO | WO-2006/032653 | 3/2006 |
| WO | WO-2006/051466 | 5/2006 |
| WO | WO-2006/064397 | 6/2006 |
| WO | WO-2006/079114 | 7/2006 |
| WO | WO-2006/118947 | 11/2006 |
| WO | WO-2006/124099 | 11/2006 |
| WO | WO-2007/007459 | 1/2007 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/056638 | 5/2007 |
| WO | WO-2007/097754 | 8/2007 |
| WO | WO-2007/101223 | 9/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |
| WO | WO-2008/021913 | 2/2008 |
| WO | WO-2008/042760 | 4/2008 |
| WO | WO-2008/086541 | 7/2008 |
| WO | WO-2008/128210 | 10/2008 |
| WO | WO-2008/130896 | 10/2008 |
| WO | WO-2008/130897 | 10/2008 |
| WO | WO-2008/130898 | 10/2008 |
| WO | WO-2008/143943 | 11/2008 |
| WO | WO-2009/018058 | 2/2009 |
| WO | WO-2009/086216 | 7/2009 |
| WO | WO-2009/096992 | 8/2009 |
| WO | WO-2009/097594 | 8/2009 |
| WO | WO-2011/022418 | 2/2011 |
| WO | WO-2010/077329 | 7/2012 |

OTHER PUBLICATIONS

(56) References Cited

OTHER PUBLICATIONS

Garg et al. Improvement in Glycemic Excursions with a Transcutaneous, Real-Time Continuous Glucose Sensor Diabetes Care, vol. 29, pp. 44-50 (Jan. 2006).*
Boyne et al. Timing of Changes in Interstitial and Venous Blood Clucose Measured Wigh a Continuous Subcutaneous Glucose Sensor Diabetes vol. 52, pp. 2790-2794 (2003).*
Armour, J. C., et al., "Application of Chronic Intravascular Blood Glucose Sensor in Dogs",*Diabetes*, vol. 39, 1990, pp. 1519-1526.
Bennion, N., et al., "Alternate Site Glucose Testing: A Crossover Design", *Diabetes Technology & Therapeutics*, vol. 4, No. 1, 2002, pp. 25-33.
Blank, T. B., et al., "Clinical Results From a Non-Invasive Blood Glucose Monitor", *Optical Diagnostics and Sensing of Biological Fluids and Glucose and Cholesterol Monitoring II, Proceeding of SPIE*, vol. 4324, 2002, pp. 1-10.
Brooks, S. L., et al., "Development of an On-Line Glucose Sensor for Fermentation Monitoring", *Biosensors*, vol. 3, 1987/88, pp. 45-56.
Cass, A. E., et al., "Ferrocene-Medicated Enzyme Electrode for Amperometric Determination of Glucose", *Analytical Chemistry*, vol. 56, No. 4, 1984, 667-671.
Csoregi, E., et al., "Design and Optimization of Selective Subcutaneously Implantable Glucose Electrode Based 'Wired' Glucose Oxidase", *Analytical Chemistry*, vol. 67, No. 7, 1995, pp. 1240-1244.
El-Khatib, F. H, et al., "Adaptive Closed-Loop Control Provides Blood-Glucose Regulation Using Subcutaneous Insulin and Glucagon Infusion in Diabetic Swine", *Journal of Diabetes Science and Technolgy*, vol. 1, No. 2, 2007, pp. 181-192.
Feldman, B., et al., "A Continuous Glucose Sensor Based on Wired Enzyme™—Results from a 3-Day Trial in Patients with Type 1 Diabetes", *Diabetes Technology & Therapeutics*, vol. 5, No. 5, 2003, pp. 769-779.
Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphet*, 2004.
Isermann, R., "Supervision, Fault-Detection and Fault-Diagnosis Methods—An Introduction", *Control Engineering Practice*, vol. 5, No. 5, 1997, pp. 639-652.
Isermann, R., et al., "Trends in the Application of Model-Based Fault Detection and Diagnosis of Technical Processes", *Control Engineering Practice*, vol. 5, No. 5, 1997, pp. 709-719.
Johnson, P. C., "Peripheral Circulation", *John Wiley & Sons*, 1978, pp. 198.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", *Diabetes Care*, vol. 24, No. 7, 2001, pp. 1303-1304.
Kaplan, S. M., "Wiley Electrical and Electronics Engineering Dictionary", *IEEE Press*, 2004, pp. 141, 142, 548, 549.
Lortz, J., et al., "What is Bluetooth? We Explain the Newest Short-Range Connectivity Technology", *Smart Computing Learning Series, Wireless Computing*, vol. 8, Issue 5, 2002, pp. 72-74.
Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.
McGarraugh, G., et al., "Glucose Measurements Using Blood Extracted from the Forearm and the Finger", *TheraSense, Inc.*, 2001, 16 Pages.
McGarraugh, G., et al., "Physiological Influences on Off-Finger Glucose Testing", *Diabetes Technology & Therapeutics*, vol. 3, No. 3, 2001, pp. 367-376.
McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensors: Choosing the Appropriate Sensing Strategy", *Biosensors*, vol. 3, 1987/88, pp. 335-346.
Pickup, J., et al., "In Vivo Molecular Sensing in Diabetes Mellitus: An Implantable Glucose Sensor with Direct Electron Transfer", *Diabetologia*, vol. 32, 1989, pp. 213-217.
Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.
Quinn, C. P., et al., "Kinetics of Glucose Delivery to Subcutaneous Tissue in Rats Measured with 0.3-mm Amperometric Microsensors", *The American Physiological Society*, 1995, E155-E161.
Roe, J. N., et al., "Bloodless Glucose Measurements", *Critical Review in Therapeutic Drug Carrier Systems*, vol. 15, Issue 3, 1998, pp. 19-241.
Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.
Salehi, C., et al., "A Telemetry-Instrumentation System for Long-Term Implantable Glucose and Oxygen Sensors", *Analytical Letters*, vol. 29, No. 13, 1996, pp. 2289-2308.
Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.
Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.
Shichiri, M., et al., "Glycaemic Control in Pancreatectomized Dogs with a Wearable Artificial Endocrine Pancreas", *Diabetologia*, vol. 24, 1983, pp. 179-184.
Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.
Shichiri, M., et al., "Membrane Design for Extending the Long-Life of an Implantable Glucose Sensor", *Diabetes Nutrition and Metabolism*, vol. 2, 1989, pp. 309-313.
Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", *Diabetes Care*, 3, vol. 9, No. 3, 1986, pp. 298-301.
Shichiri, M., et al., "Wearable Artificial Endocrine Pancreas With Needle-Type Glucose Sensor", *The Lancet*, 1982, pp. 1129-1131.
Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.
Sternberg, R., et al., "Study and Development of Multilayer Needle-Type Enzyme-Based Glucose Microsensors", *Biosensors*, vol. 4, 1988, pp. 27-40.
Thompson, M., et al., "In Vivo Probes: Problems and Perspectives", *Clinical Biochemistry*, vol. 19, 1986, pp. 255-261.
Turner, A., et al., "Diabetes Mellitus: Biosensors for Research and Management", *Biosensors*, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.
Velho, G., et al., "Strategies for Calibrating a Subcutaneous Glucose Sensor", *Biomedica Biochimica Acta*, vol. 48, 1989, pp. 957-964.
Wilson, G. S., et al., "Progress Toward the Development of an Implantable Sensor for Glucose", *Clinical Chemistry*, vol. 38, No. 9, 1992, pp. 1613-1617.

(56) References Cited

OTHER PUBLICATIONS

PCT Application No. PCT/US2008/006247, International Preliminary Report on Patentability and Written Opinion of the International Searching Authority mailed Nov. 26, 2009.
PCT Application No. PCT/US2008/006247, International Search Report and Written Opinion of the International Searching Authority mailed Sep. 5, 2008.
PCT Application No. PCT/US2008/060277, International Preliminary Report on Patentability and Written Opinion of the International Searching Authority mailed Oct. 29, 2009.
PCT Application No. PCT/US2008/060277, International Search Report and Written Opinion of the International Searching Authority mailed Sep. 22, 2008.
PCT Application No. PCT/US2008/060279, International Preliminary Report on Patentability and Written Opinion of the International Searching Authority mailed Oct. 29, 2009.
PCT Application No. PCT/US2008/060279, International Search Report and Written Opinion of the International Searching Authority mailed Jul. 14, 2008.
PCT Application No. PCT/US2008/060281, International Preliminary Report on Patentability and Written Opinion of the International Searching Authority mailed Oct. 29, 2009.
PCT Application No. PCT/US2008/060282, International Preliminary Report on Patentability and Written Opinion of the International Searching Authority mailed Oct. 29, 2009.
PCT Application No. PCT/US2008/060282, International Search Report and Written Opinion of the International Searching Authority mailed Jun. 18, 2009.
PCT Application No. PCT/US2008/060284, International Preliminary Report on Patentability and Written Opinion of the International Searching Authority mailed Oct. 29, 2009.
PCT Application No. PCT/US2008/060284, International Search Report and Written Opinion of the International Searching Authority mailed Sep. 23, 2008.
PCT Application No. PCT/US2008/070923, International Preliminary Report on Patentability and Written Opinion of the International Searching Authority, mailed Feb. 11, 2010.
PCT Application No. PCT/US2008/070923, International Search Report and Written Opinion of the International Searching Authority mailed Oct. 1, 2008.
U.S. Appl. No. 11/831,866, Office Action mailed Jun. 25, 2009.
U.S. Appl. No. 11/831,866, Supplemental Office Action mailed Dec. 9, 2009.
U.S. Appl. No. 12/102,839, Office Action mailed Aug. 5, 2010.
U.S. Appl. No. 12/102,839, Office Action mailed Dec. 14, 2009.
International Search Report and Written Opinion of the International Searching Authority for PCT Application No. PCT/US2008/060281 filed Apr. 14, 2008 to Abbott Diabetes Care, Inc., mailed Sep. 23, 2008.
Mougiakakou, et al., "A Real Time Simulation Model of Glucose-Insulin Metabolism for Type 1 Diabetes Patients", *Proceedings of the 2005 IEEE*, 2005, pp. 298-301.
U.S. Appl. No. 11/831,881, Office Action mailed Jun. 21, 2011.
U.S. Appl. No. 11/831,895, Office Action mailed May 25, 2011.
U.S. Appl. No. 11/831,895, Office Action mailed Oct. 14, 2011.
U.S. Appl. No. 12/102,839, Office Action mailed Jan. 25, 2011.
U.S. Appl. No. 12/102,839, Office Action mailed Oct. 27, 2011.
U.S. Appl. No. 12/102,844, Office Action mailed Aug. 17, 2011.
U.S. Appl. No. 12/102,855, Office Action mailed Aug. 24, 2011.
U.S. Appl. No. 12/102,856, Office Action mailed Aug. 17, 2011.
U.S. Appl. No. 12/152,623, Notice of Allowance Mailed Nov. 3, 2011.
U.S. Appl. No. 12/152,623, Office Action mailed May 26, 2011.
U.S. Appl. No. 12/152,636, Office Action mailed Dec. 27, 2010.
U.S. Appl. No. 12/152,636, Office Action mailed Sep. 20, 2011.
U.S. Appl. No. 12/152,648, Office Action mailed Aug. 12, 2011.
U.S. Appl. No. 12/152,649, Office Action mailed Aug. 5, 2011.
U.S. Appl. No. 12/152,650, Office Action mailed Aug. 11, 2011.
U.S. Appl. No. 12/152,652, Office Action mailed Jun. 23, 2011.
U.S. Appl. No. 12/152,652, Office Action mailed Nov. 1, 2011.
U.S. Appl. No. 12/152,657, Office Action mailed Aug. 11, 2011.
U.S. Appl. No. 12/152,662, Office Action mailed Aug. 19, 2011.
U.S. Appl. No. 12/152,670, Notice of Allowance mailed Jun. 20, 2011.
U.S. Appl. No. 12/152,670, Office Action mailed Jan. 7, 2011.
U.S. Appl. No. 12/152,673 Office Action mailed Aug. 26, 2011.
European Patent Application No. 08745805.5, Extended European Search Report mailed May 23, 2012.
U.S. Appl. No. 11/831,881, Office Action mailed Nov. 17, 2011.
U.S. Appl. No. 11/831,895, Advisory Action mailed Jan. 18, 2012.
U.S. Appl. No. 11/831,895, Advisory Action mailed Jan. 25, 2012.
U.S. Appl. No. 12/102,839, Office Action mailed May 25, 2012.
U.S. Appl. No. 12/102,844, Notice of Allowance mailed Jan. 10, 2012.
U.S. Appl. No. 12/102,855, Office Action mailed Jan. 10, 2012.
U.S. Appl. No. 12/102,856, Office Action mailed Jan. 10, 2012.
U.S. Appl. No. 12/152,636, Advisory Action mailed Jan. 19, 2012.
U.S. Appl. No. 12/152,636, Advisory Action mailed Jan. 6, 2012.
U.S. Appl. No. 12/152,636, Notice of Allowance mailed Jun. 19, 2012.
U.S. Appl. No. 12/152,648, Office Action mailed Jan. 27, 2012.
U.S. Appl. No. 12/152,649, Office Action mailed Jan. 27, 2012.
U.S. Appl. No. 12/152,650, Office Action mailed Jan. 26, 2012.
U.S. Appl. No. 12/152,652, Advisory Action mailed Jan. 13, 2012.
U.S. Appl. No. 12/152,652, Notice of Allowance mailed May 3, 2012.
U.S. Appl. No. 12/152,657, Office Action mailed Jan. 26, 2012.
U.S. Appl. No. 12/152,662, Office Action mailed Jan. 11, 2012.
U.S. Appl. No. 12/152,673, Office Action mailed Jan. 5, 2012.
European Patent Application No. 08745807.1, Extended European Search Report mailed Oct. 8, 2012.
Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.
Parker, R., et al., "Robust H∞ Glucose Control in Diabetes Using a Physiological Model", *AIChE Journal*, vol. 46, No. 12, 2000, pp. 2537-2549.
European Patent Application No. 08745803.0, Extended European Search Report mailed Sep. 27, 2012.
European Patent Application No. 08745809.7, Extended European Search Report mailed Jul. 2, 2012.
European Patent Application No. 08754499.5, Extended European Search Report mailed Sep. 20, 2012.
European Patent Application No. 08871628.7 Extended European Search Report mailed Nov. 2, 2012.
U.S. Appl. No. 11/831,881, Office Action mailed Oct. 1, 2012.
U.S. Appl. No. 11/831,895, Office Action mailed Jul. 20, 2012.
U.S. Appl. No. 12/152,648, Office Action mailed Aug. 29, 2012.
U.S. Appl. No. 12/152,649, Office Action mailed Nov. 5, 2012.
U.S. Appl. No. 12/152,650, Office Action mailed Jul. 25, 2012.
U.S. Appl. No. 12/152,673, Office Action mailed Jul. 11, 2012.
U.S. Appl. No. 13/356,598, Office Action mailed Aug. 30, 2012.
Bremer, T. M., et al., "Benchmark Data from the Literature for Evaluation of New Glucose Sensing Technologies", *Diabetes Technology & Therapeutics*, vol. 3, No. 3, 2001, pp. 409-418.
Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.
Kuure-Kinsey, M., et al., "A Dual-Rate Kalman Filter for Continuous Glucose Monitoring", *Proceedings of the 28th IEEE, EMBS Annual International Conference*, New York City, 2006, pp. 63-66.
Li, Y., et al., "In Vivo Release From a Drug Delivery MEMS Device", *Journal of Controlled Release*, vol. 100, 2004, 99.211-219.
Lo, B., et al., "Key Technical Challenges and Current Implementations of Body Sensor Networks", *Body Sensor Networks*, 2005, pp. 1-5.
Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.

(56) References Cited

OTHER PUBLICATIONS

Panteleon, A. E., et al., "The Role of the Independent Variable to Glucose Sensor Calibration", *Diabetes Technology & Therapeutics*, vol. 5, No. 3, 2003, pp. 401-410.
Rodriguez, N., et al., "Flexible Communication and Control Protocol for Injectable Neuromuscular Interfaces", *IEEE Transactions on Biomedical Circuits and Systems*, vol. 1, No. 1, 2007, pp. 19-27.
U.S. Appl. No. 11/831,881, Advisory Action mailed Aug. 23, 2013.
U.S. Appl. No. 11/831,895, Advisory Action mailed Aug. 5, 2013.
U.S. Appl. No. 11/831,895, Office Action mailed May 16, 2013.
U.S. Appl. No. 11/831,895, Office Action mailed Oct. 1, 2013.
U.S. Appl. No. 12/102,839, Advisory Action mailed May 1, 2013.
U.S. Appl. No. 12/102,839, Office Action mailed Aug. 1, 2013.
U.S. Appl. No. 12/102,839, Office Action mailed Dec. 14, 2012.
U.S. Appl. No. 12/102,839, Office Action mailed Dec. 5, 2013.
U.S. Appl. No. 12/102,855, Office Action mailed Jun. 11, 2014.
U.S. Appl. No. 12/102,856, Office Action mailed May 7, 2014.
U.S. Appl. No. 12/152,648, Notice of Allowance mailed Aug. 2, 2013.
U.S. Appl. No. 12/152,648, Office Action mailed Mar. 13, 2013.
U.S. Appl. No. 12/152,649, Notice of Allowance mailed Jul. 1, 2013.
U.S. Appl. No. 12/152,650, Notice of Allowance mailed Jan. 22, 2013.
U.S. Appl. No. 12/152,662, Office Action mailed Jun. 12, 2014.
U.S. Appl. No. 12/152,673, Advisory Action mailed Apr. 9, 2013.
U.S. Appl. No. 12/152,673, Office Action mailed Jan. 30, 2013.
U.S. Appl. No. 13/356,598, Notice of Allowance mailed Jul. 11, 2013.
U.S. Appl. No. 13/356,598, Office Action mailed May 2, 2013.
U.S. Appl. No. 13/567,038, Notice of Allowance Nov. 22, 2013.
U.S. Appl. No. 13/567,038, Office Action mailed Jun. 6, 2013.
U.S. Appl. No. 13/567,038, Office Action mailed Oct. 10, 2013.
U.S. Appl. No. 13/599,847, Notice of Allowance mailed Aug. 21, 2013.
U.S. Appl. No. 13/599,847, Office Action mailed Jan. 29, 2013.
Arnold, M. A., et al., "Selectivity Assessment of Noninvasive Glucose Measurements Based on Analysis of Mulivariate Calibration Vectors", *Journal of Diabetes Science and Technology*, vol. 1, No. 4, 2007, pp. 454-462.
Eren-Oruklu, M., et al., "Estimation of Future Glucose Concentrations with Subject-Specific Recursive Linear Models", *Diabetes Technology & Therapeutics* vol. 11(4), 2009, pp. 243-253.
Canadian Patent Application No. 2,683,930, Examiner's Report mailed Jul. 22, 2014.
U.S. Appl. No. 11/831,881, Notice of Allowance mailed Jun. 20, 2014.
U.S. Appl. No. 11/831,881, Office Action mailed Mar. 13, 2014.
U.S. Appl. No. 11/831,881, Office Action mailed May 23, 2013.
U.S. Appl. No. 11/831,895, Office Action mailed Jul. 17, 2014.
U.S. Appl. No. 12/102,855, Office Action mailed Oct. 24, 2014.
U.S. Appl. No. 12/102,856, Office Action mailed Nov. 25, 2014.
U.S. Appl. No. 12/152,657, Office Action mailed Sep. 18, 2014.
U.S. Appl. No. 12/152,662, Advisory Action mailed Sep. 3, 2014.
U.S. Appl. No. 14/106,000, Office Action mailed Aug. 26, 2014.
U.S. Appl. No. 14/106,000, Office Action mailed Jun. 17, 2014.
U.S. Appl. No. 14/106,000, Office Action mailed Nov. 26, 2014.

\* cited by examiner

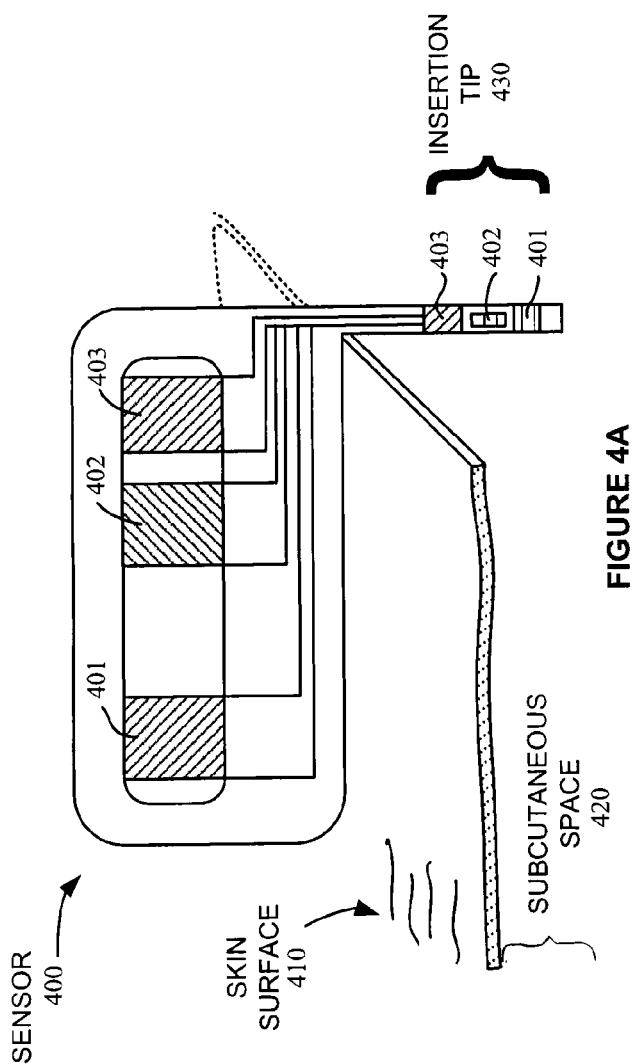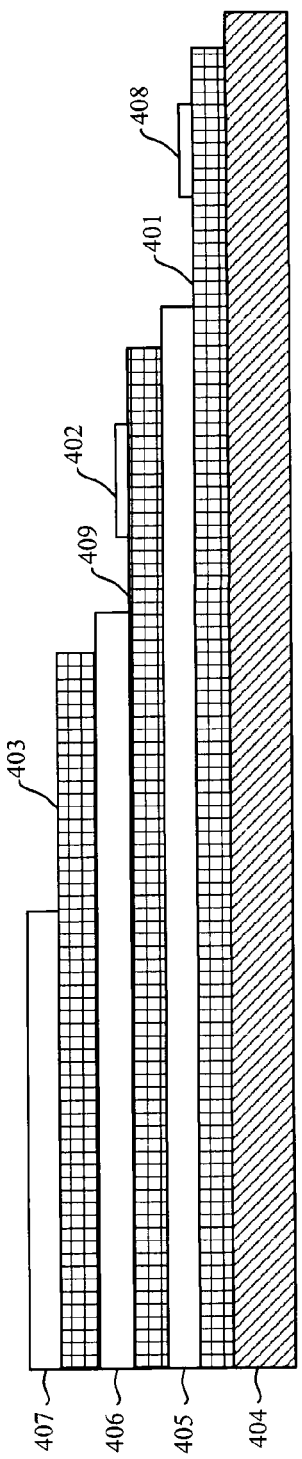

METHOD AND APPARATUS FOR PROVIDING DATA PROCESSING AND CONTROL IN MEDICAL COMMUNICATION SYSTEM

RELATED APPLICATIONS

The present application claims priority under §35 U.S.C. 119(e) to U.S. provisional application No. 60/911,872 filed Apr. 14, 2007, entitled "Method and Apparatus for Providing Data Processing and Control in Medical Communication System", and assigned to the Assignee of the present application, Abbott Diabetes Care Inc. of Alameda, Calif., the disclosure of which is incorporated herein by reference for all purposes.

BACKGROUND

Analyte, e.g., glucose monitoring systems including continuous and discrete monitoring systems generally include a small, lightweight battery powered and microprocessor controlled system which is configured to detect signals proportional to the corresponding measured glucose levels using an electrometer, and RF signals to transmit the collected data. One aspect of certain analyte monitoring systems include a transcutaneous or subcutaneous analyte sensor configuration which is, for example, partially mounted on the skin of a subject whose analyte level is to be monitored. The sensor cell may use a two or three-electrode (work, reference and counter electrodes) configuration driven by a controlled potential (potentiostat) analog circuit connected through a contact system.

The analyte sensor may be configured so that a portion thereof is placed under the skin of the patient so as to detect the analyte levels of the patient, and another portion of segment of the analyte sensor that is in communication with the transmitter unit. The transmitter unit is configured to transmit the analyte levels detected by the sensor over a wireless communication link such as an RF (radio frequency) communication link to a receiver/monitor unit. The receiver/monitor unit performs data analysis, among others on the received analyte levels to generate information pertaining to the monitored analyte levels. To provide flexibility in analyte sensor manufacturing and/or design, among others, tolerance of a larger range of the analyte sensor sensitivities for processing by the transmitter unit is desirable.

In view of the foregoing, it would be desirable to have a method and system for providing data processing and control for use in medical telemetry systems such as, for example, analyte monitoring systems.

SUMMARY OF THE INVENTION

In one embodiment, method and apparatus for receiving a signal associated with an analyte level of a user, determining whether the received signal deviates from a predetermined signal characteristic, determining an operational state associated with an analyte monitoring device, comparing a prior signal associated with the analyte level of the user to the received signal, presenting an output data associated with the operational state of the analyte monitoring device based, at least in part, on one or more of the received signal or the prior signal, and receiving a user input data based on the presented output data, is disclosed.

These and other objects, features and advantages of the present invention will become more fully apparent from the following detailed description of the embodiments, the appended claims and the accompanying drawings.

BRIEF DESCRIPTION OF THE DRAWINGS

FIGS. 4A-4B illustrate a perspective view and a cross sectional view, respectively of an analyte sensor in accordance with one embodiment of the present invention;

DETAILED DESCRIPTION

As described in further detail below, in accordance with the various embodiments of the present invention, there is provided a method and apparatus for providing data processing and control for use in a medical telemetry system. In particular, within the scope of the present invention, there is provided a method and system for providing data communication and control for use in a medical telemetry system such as, for example, a continuous glucose monitoring system.

Figure 1:
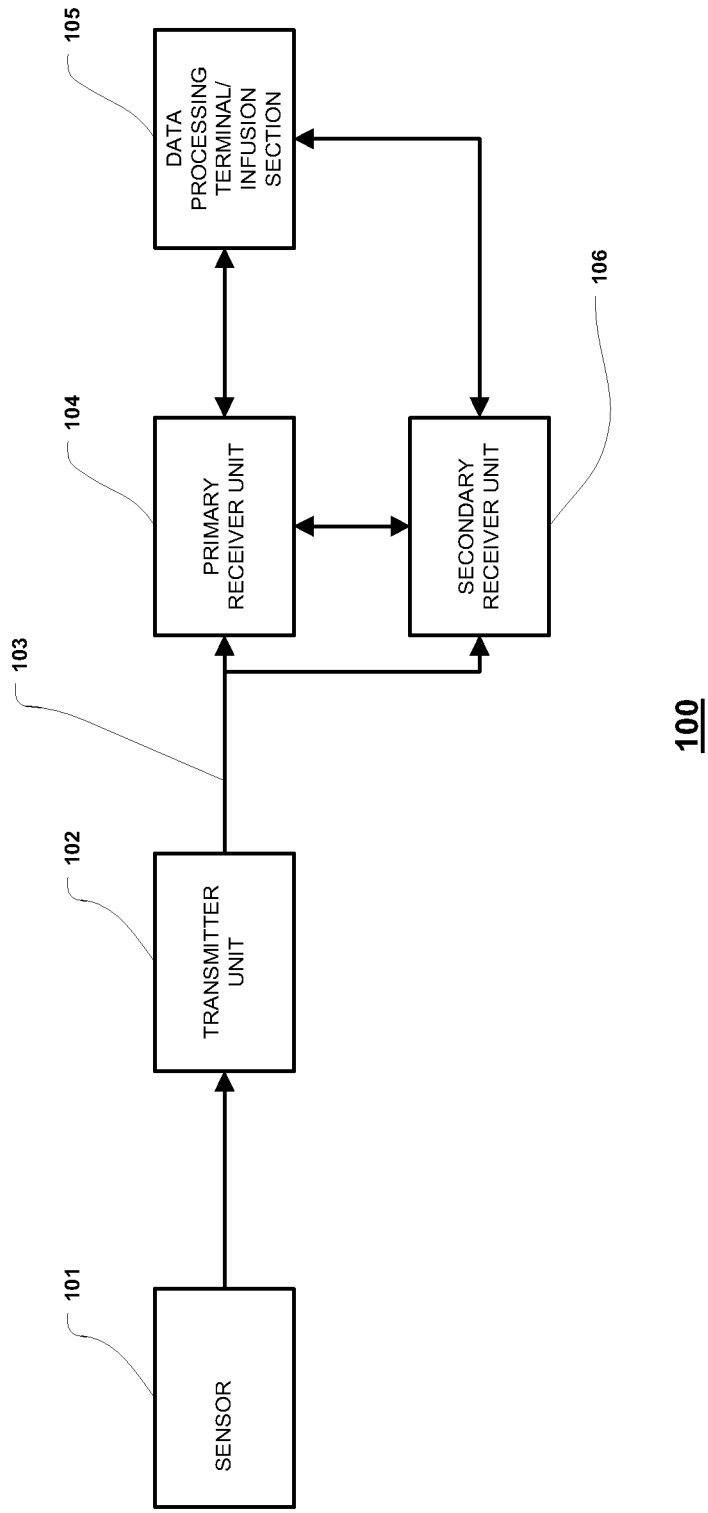
FIG. 1 illustrates a block diagram of a data monitoring and management system for practicing one or more embodiments of the present invention.

FIG. 1 illustrates a data monitoring and management system such as, for example, analyte (e.g., glucose) monitoring system 100 in accordance with one embodiment of the present invention. The subject invention is further described primarily with respect to a glucose monitoring system for convenience and such description is in no way intended to limit the scope of the invention. It is to be understood that the analyte monitoring system may be configured to monitor a variety of analytes, e.g., lactate, and the like.

Analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored.

The analyte monitoring system 100 includes a sensor 101, a transmitter unit 102 coupled to the sensor 101, and a primary receiver unit 104 which is configured to communicate with the transmitter unit 102 via a communication link 103. The primary receiver unit 104 may be further configured to transmit data to a data processing terminal 105 for evaluating the data received by the primary receiver unit 104. Moreover, the data processing terminal 105 in one embodiment may be configured to receive data directly from the transmitter unit 102 via a communication link which may optionally be configured for bi-directional communication.

Also shown in FIG. 1 is a secondary receiver unit 106 which is operatively coupled to the communication link and configured to receive data transmitted from the transmitter unit 102. Moreover, as shown in the Figure, the secondary receiver unit 106 is configured to communicate with the primary receiver unit 104 as well as the data processing terminal 105. Indeed, the secondary receiver unit 106 may be configured for bi-directional wireless communication with each of the primary receiver unit 104 and the data processing terminal 105. As discussed in further detail below, in one embodiment of the present invention, the secondary receiver unit 106 may be configured to include a limited number of functions and features as compared with the primary receiver unit 104. As such, the secondary receiver unit 106 may be configured substantially in a smaller compact housing or embodied in a device such as a wrist watch, for example. Alternatively, the secondary receiver unit 106 may be configured with the same or substantially similar functionality as the primary receiver unit 104, and may be configured to be used in conjunction with a docking cradle unit for placement by bedside, for night time monitoring, and/or bi-directional communication device.

Only one sensor 101, transmitter unit 102, communication link 103, and data processing terminal 105 are shown in the embodiment of the analyte monitoring system 100 illustrated in FIG. 1. However, it will be appreciated by one of ordinary skill in the art that the analyte monitoring system 100 may include one or more sensor 101, transmitter unit 102, communication link 103, and data processing terminal 105. Moreover, within the scope of the present invention, the analyte monitoring system 100 may be a continuous monitoring system, or semi-continuous, or a discrete monitoring system. In a multi-component environment, each device is configured to be uniquely identified by each of the other devices in the system so that communication conflict is readily resolved between the various components within the analyte monitoring system 100.

In one embodiment of the present invention, the sensor 101 is physically positioned in or on the body of a user whose analyte level is being monitored. The sensor 101 may be configured to continuously sample the analyte level of the user and convert the sampled analyte level into a corresponding data signal for transmission by the transmitter unit 102. In one embodiment, the transmitter unit 102 is coupled to the sensor 101 so that both devices are positioned on the user's body, with at least a portion of the analyte sensor 101 positioned transcutaneously under the skin layer of the user. The transmitter unit 102 performs data processing such as filtering and encoding on data signals, each of which corresponds to a sampled analyte level of the user, for transmission to the primary receiver unit 104 via the communication link 103.

In one embodiment, the analyte monitoring system 100 is configured as a one-way RF communication path from the transmitter unit 102 to the primary receiver unit 104. In such embodiment, the transmitter unit 102 transmits the sampled data signals received from the sensor 101 without acknowledgement from the primary receiver unit 104 that the transmitted sampled data signals have been received. For example, the transmitter unit 102 may be configured to transmit the encoded sampled data signals at a fixed rate (e.g., at one minute intervals) after the completion of the initial power on procedure. Likewise, the primary receiver unit 104 may be configured to detect such transmitted encoded sampled data signals at predetermined time intervals. Alternatively, the analyte monitoring system 100 may be configured with a bi-directional RF (or otherwise) communication between the transmitter unit 102 and the primary receiver unit 104.

Additionally, in one aspect, the primary receiver unit 104 may include two sections. The first section is an analog interface section that is configured to communicate with the transmitter unit 102 via the communication link 103. In one embodiment, the analog interface section may include an RF receiver and an antenna for receiving and amplifying the data signals from the transmitter unit 102, which are thereafter, demodulated with a local oscillator and filtered through a band-pass filter. The second section of the primary receiver unit 104 is a data processing section which is configured to process the data signals received from the transmitter unit 102 such as by performing data decoding, error detection and correction, data clock generation, and data bit recovery.

In operation, upon completing the power-on procedure, the primary receiver unit 104 is configured to detect the presence of the transmitter unit 102 within its range based on, for example, the strength of the detected data signals received from the transmitter unit 102 or a predetermined transmitter identification information. Upon successful synchronization with the corresponding transmitter unit 102, the primary receiver unit 104 is configured to begin receiving from the transmitter unit 102 data signals corresponding to the user's detected analyte level. More specifically, the primary receiver unit 104 in one embodiment is configured to perform synchronized time hopping with the corresponding synchronized transmitter unit 102 via the communication link 103 to obtain the user's detected analyte level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected analyte level of the user.

Within the scope of the present invention, the data processing terminal 105 may include an infusion device such as an insulin infusion pump or the like, which may be configured to administer insulin to patients, and which may be configured to communicate with the receiver unit 104 for receiving, among others, the measured analyte level. Alternatively, the receiver unit 104 may be configured to integrate an infusion device therein so that the receiver unit 104 is configured to administer insulin therapy to patients, for example, for administering and modifying basal profiles, as well as for determining appropriate boluses for administration based on, among others, the detected analyte levels received from the transmitter unit 102.

Additionally, the transmitter unit 102, the primary receiver unit 104 and the data processing terminal 105 may each be configured for bi-directional wireless communication such that each of the transmitter unit 102, the primary receiver unit 104 and the data processing terminal 105 may be configured to communicate (that is, transmit data to and receive data from) with each other via the wireless communication link 103. More specifically, the data processing terminal 105 may in one embodiment be configured to receive data directly from the transmitter unit 102 via a communication link, where the communication link, as described above, may be configured for bi-directional communication.

In this embodiment, the data processing terminal 105 which may include an insulin pump, may be configured to receive the analyte signals from the transmitter unit 102, and thus, incorporate the functions of the receiver 104 including data processing for managing the patient's insulin therapy and analyte monitoring. In one embodiment, the communication link 103 may include one or more of an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements) while avoiding potential data collision and interference.

Figure 2:
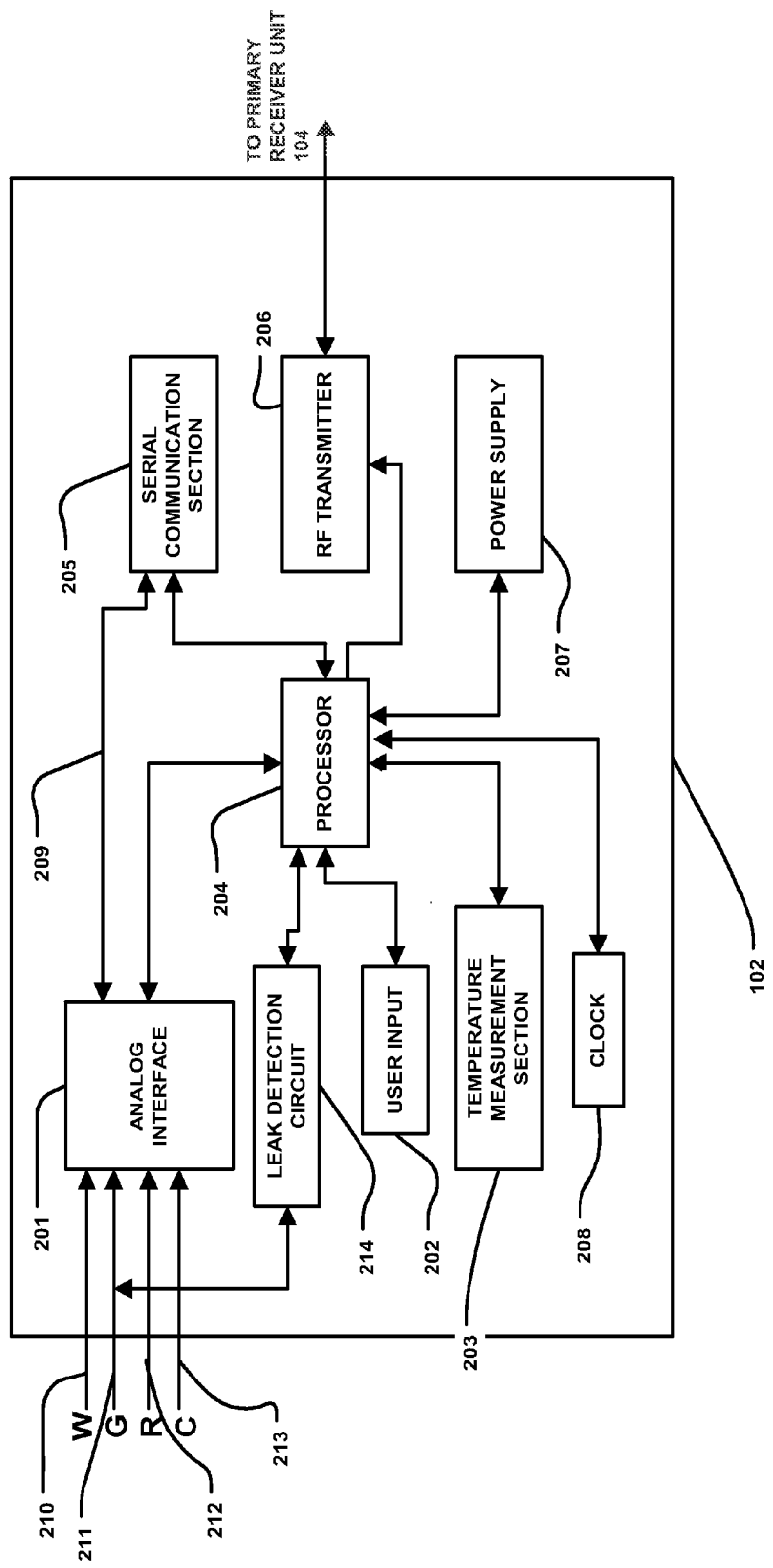
FIG. 2 is a block diagram of the transmitter unit of the data monitoring and management system shown in FIG. 1 in accordance with one embodiment of the present invention.

FIG. 2 is a block diagram of the transmitter of the data monitoring and detection system shown in FIG. 1 in accordance with one embodiment of the present invention. Referring to the Figure, the transmitter unit 102 in one embodiment includes an analog interface 201 configured to communicate with the sensor 101 (FIG. 1), a user input 202, and a temperature detection section 203, each of which is operatively coupled to a transmitter processor 204 such as a central processing unit (CPU).

Further shown in FIG. 2 are a transmitter serial communication section 205 and an RF transmitter 206, each of which is also operatively coupled to the transmitter processor 204. Moreover, a power supply 207 such as a battery is also provided in the transmitter unit 102 to provide the necessary power for the transmitter unit 102. Additionally, as can be seen from the Figure, clock 208 is provided to, among others, supply real time information to the transmitter processor 204.

As can be seen from FIG. 2, the sensor 101 (FIG. 1) is provided four contacts, three of which are electrodes—work electrode (W) 210, guard contact (G) 211, reference electrode (R) 212, and counter electrode (C) 213, each operatively coupled to the analog interface 201 of the transmitter unit 102. In one embodiment, each of the work electrode (W) 210, guard contact (G) 211, reference electrode (R) 212, and counter electrode (C) 213 may be made using a conductive material that is either printed or etched, for example, such as carbon which may be printed, or metal foil (e.g., gold) which may be etched, or alternatively provided on a substrate material using laser or photolithography.

In one embodiment, a unidirectional input path is established from the sensor 101 (FIG. 1) and/or manufacturing and testing equipment to the analog interface 201 of the transmitter unit 102, while a unidirectional output is established from the output of the RF transmitter 206 of the transmitter unit 102 for transmission to the primary receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter unit 102 is configured to transmit to the primary receiver unit 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter unit 102 for operation upon completion of the manufacturing process as well as for direct communication for diagnostic and testing purposes.

As discussed above, the transmitter processor 204 is configured to transmit control signals to the various sections of the transmitter unit 102 during the operation of the transmitter unit 102. In one embodiment, the transmitter processor 204 also includes a memory (not shown) for storing data such as the identification information for the transmitter unit 102, as well as the data signals received from the sensor 101. The stored information may be retrieved and processed for transmission to the primary receiver unit 104 under the control of the transmitter processor 204. Furthermore, the power supply 207 may include a commercially available battery.

The transmitter unit 102 is also configured such that the power supply section 207 is capable of providing power to the transmitter for a minimum of about three months of continuous operation after having been stored for about eighteen months in a low-power (non-operating) mode. In one embodiment, this may be achieved by the transmitter processor 204 operating in low power modes in the non-operating state, for example, drawing no more than approximately 1 µA of current. Indeed, in one embodiment, the final step during the manufacturing process of the transmitter unit 102 may place the transmitter unit 102 in the lower power, non-operating state (i.e., post-manufacture sleep mode). In this manner, the shelf life of the transmitter unit 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present invention, the power supply unit 207 is configured to provide the necessary power to each of the components of the transmitter unit 102 shown in FIG. 2.

Referring back to FIG. 2, the power supply section 207 of the transmitter unit 102 in one embodiment may include a rechargeable battery unit that may be recharged by a separate power supply recharging unit (for example, provided in the receiver unit 104) so that the transmitter unit 102 may be powered for a longer period of usage time. Moreover, in one embodiment, the transmitter unit 102 may be configured without a battery in the power supply section 207, in which case the transmitter unit 102 may be configured to receive power from an external power supply source (for example, a battery) as discussed in further detail below.

Referring yet again to FIG. 2, the temperature detection section 203 of the transmitter unit 102 is configured to monitor the temperature of the skin near the sensor insertion site. The temperature reading is used to adjust the analyte readings obtained from the analog interface 201. The RF transmitter 206 of the transmitter unit 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the primary receiver unit 104.

Referring yet again to FIG. 2, also shown is a leak detection circuit 214 coupled to the guard contact (G) 211 and the processor 204 in the transmitter unit 102 of the data monitoring and management system 100. The leak detection circuit 214 in accordance with one embodiment of the present invention may be configured to detect leakage current in the sensor 101 to determine whether the measured sensor data are corrupt or whether the measured data from the sensor 101 is accurate.

Figure 3:
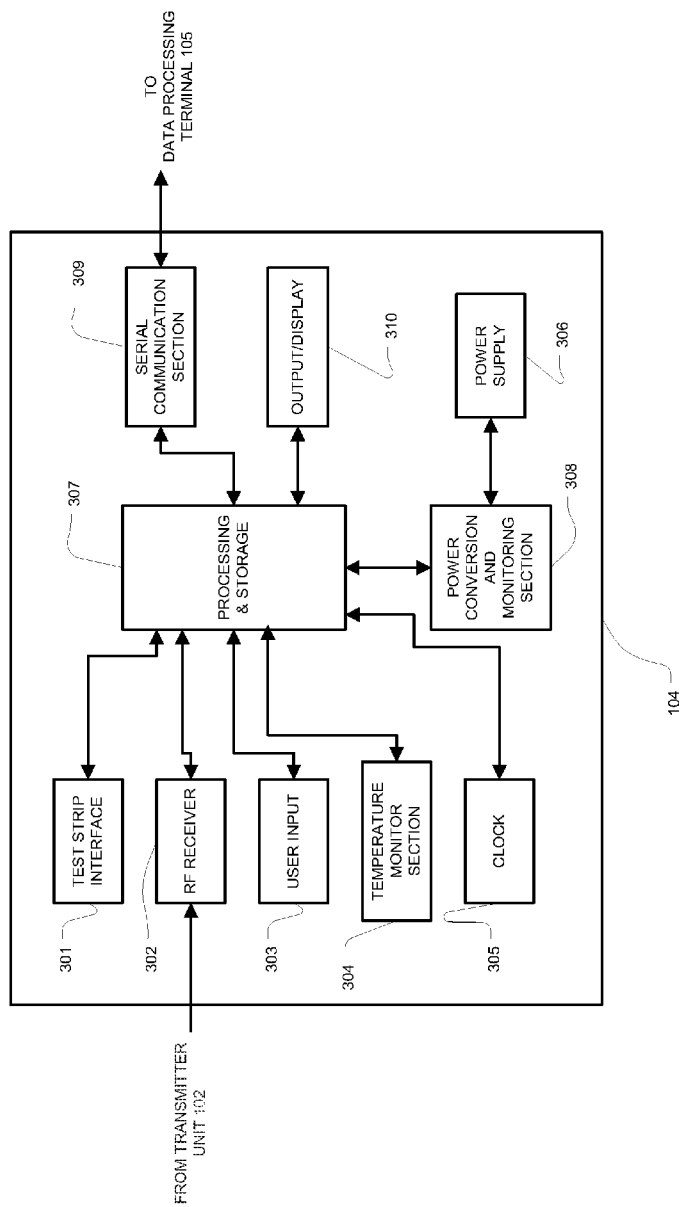
FIG. 3 is a block diagram of the receiver/monitor unit of the data monitoring and management system shown in FIG. 1 in accordance with one embodiment of the present invention.

FIG. 3 is a block diagram of the receiver/monitor unit of the data monitoring and management system shown in FIG. 1 in accordance with one embodiment of the present invention. Referring to FIG. 3, the primary receiver unit 104 includes a blood glucose test strip interface 301, an RF receiver 302, an input 303, a temperature detection section 304, and a clock 305, each of which is operatively coupled to a receiver processor 307. As can be further seen from the Figure, the primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the receiver processor 307.

In one embodiment, the test strip interface 301 includes a glucose level testing portion to receive a manual insertion of a glucose test strip, and thereby determine and display the glucose level of the test strip on the output 310 of the primary receiver unit 104. This manual testing of glucose can be used to calibrate sensor 101. The RF receiver 302 is configured to communicate, via the communication link 103 (FIG. 1) with the RF transmitter 206 of the transmitter unit 102, to receive encoded data signals from the transmitter unit 102 for, among others, signal mixing, demodulation, and other data processing. The input 303 of the primary receiver unit 104 is configured to allow the user to enter information into the primary receiver unit 104 as needed. In one aspect, the input 303 may include one or more keys of a keypad, a touch-sensitive screen, or a voice-activated input command unit. The temperature detection section 304 is configured to provide temperature information of the primary receiver unit 104 to the receiver processor 307, while the clock 305 provides, among others, real time information to the receiver processor 307.

Each of the various components of the primary receiver unit 104 shown in FIG. 3 is powered by the power supply 306 which, in one embodiment, includes a battery. Furthermore, the power conversion and monitoring section 308 is configured to monitor the power usage by the various components in the primary receiver unit 104 for effective power management and to alert the user, for example, in the event of power usage which renders the primary receiver unit 104 in sub-optimal operating conditions. An example of such sub-optimal operating condition may include, for example, operating the vibration output mode (as discussed below) for a period of time thus substantially draining the power supply 306 while the processor 307 (thus, the primary receiver unit 104) is turned on. Moreover, the power conversion and monitoring section 308 may additionally be configured to include a reverse polarity protection circuit such as a field effect transistor (FET) configured as a battery activated switch.

The serial communication section 309 in the primary receiver unit 104 is configured to provide a bi-directional communication path from the testing and/or manufacturing equipment for, among others, initialization, testing, and configuration of the primary receiver unit 104. Serial communication section 309 can also be used to upload data to a computer, such as time-stamped blood glucose data. The communication link with an external device (not shown) can be made, for example, by cable, infrared (IR) or RF link. The output 310 of the primary receiver unit 104 is configured to provide, among others, a graphical user interface (GUI) such as a liquid crystal display (LCD) for displaying information. Additionally, the output 310 may also include an integrated speaker for outputting audible signals as well as to provide vibration output as commonly found in handheld electronic devices, such as mobile telephones presently available. In a further embodiment, the primary receiver unit 104 also includes an electro-luminescent lamp configured to provide backlighting to the output 310 for output visual display in dark ambient surroundings.

Referring back to FIG. 3, the primary receiver unit 104 in one embodiment may also include a storage section such as a programmable, non-volatile memory device as part of the processor 307, or provided separately in the primary receiver unit 104, operatively coupled to the processor 307. The processor 307 is further configured to perform Manchester decoding as well as error detection and correction upon the encoded data signals received from the transmitter unit 102 via the communication link 103.

In a further embodiment, the one or more of the transmitter unit 102, the primary receiver unit 104, secondary receiver unit 106, or the data processing terminal/infusion section 105 may be configured to receive the blood glucose value wirelessly over a communication link from, for example, a glucose meter. In still a further embodiment, the user or patient manipulating or using the analyte monitoring system 100 (FIG. 1) may manually input the blood glucose value using, for example, a user interface (for example, a keyboard, keypad, and the like) incorporated in the one or more of the transmitter unit 102, the primary receiver unit 104, secondary receiver unit 106, or the data processing terminal/infusion section 105.

Additional detailed description of the continuous analyte monitoring system, its various components including the functional descriptions of the transmitter are provided in U.S. Pat. No. 6,175,752 issued Jan. 16, 2001 entitled "Analyte Monitoring Device and Methods of Use", and in application Ser. No. 10/745,878 filed Dec. 26, 2003, now U.S. Pat. No. 7,811,231, entitled "Continuous Glucose Monitoring System and Methods of Use", each assigned to the Assignee of the present application.

FIGS. 4A-4B illustrate a perspective view and a cross sectional view, respectively of an analyte sensor in accordance with one embodiment of the present invention. Referring to FIG. 4A, a perspective view of a sensor 400, the major portion of which is above the surface of the skin 410, with an insertion tip 430 penetrating through the skin and into the subcutaneous space 420 in contact with the user's biofluid such as interstitial fluid. Contact portions of a working electrode 401, a reference electrode 402, and a counter electrode 403 can be seen on the portion of the sensor 400 situated above the skin surface 410. Working electrode 401, a reference electrode 402, and a counter electrode 403 can be seen at the end of the insertion tip 430.

Referring now to FIG. 4B, a cross sectional view of the sensor 400 in one embodiment is shown. In particular, it can be seen that the various electrodes of the sensor 400 as well as the substrate and the dielectric layers are provided in a stacked or layered configuration or construction. For example, as shown in FIG. 4B, in one aspect, the sensor 400 (such as the sensor 101 FIG. 1), includes a substrate layer 404, and a first conducting layer 401 such as a carbon trace disposed on at least a portion of the substrate layer 404, and which may comprise the working electrode. Also shown disposed on at least a portion of the first conducting layer 401 is a sensing layer 408.

Referring back to FIG. 4B, a first insulation layer such as a first dielectric layer 405 is disposed or stacked on at least a portion of the first conducting layer 401, and further, a second conducting layer 409 such as another carbon trace may be disposed or stacked on top of at least a portion of the first insulation layer (or dielectric layer) 405. As shown in FIG. 4B, the second conducting layer 409 may comprise the reference electrode 402, and in one aspect, may include a layer of silver/silver chloride (Ag/AgCl).

Referring still again to FIG. 4B, a second insulation layer 406 such as a dielectric layer in one embodiment may be disposed or stacked on at least a portion of the second conducting layer 409. Further, a third conducting layer 403 which may include carbon trace and that may comprise the counter electrode 403 may in one embodiment be disposed on at least a portion of the second insulation layer 406. Finally, a third insulation layer 407 is disposed or stacked on at least a portion of the third conducting layer 403. In this manner, the sensor 400 may be configured in a stacked or layered construction or configuration such that at least a portion of each of the conducting layers is separated by a respective insulation layer (for example, a dielectric layer).

Additionally, within the scope of the present invention, some or all of the electrodes 401, 402, 403 may be provided on the same side of the substrate 404 in a stacked construction as described above, or alternatively, may be provided in a co-planar manner such that each electrode is disposed on the same plane on the substrate 404, however, with a dielectric material or insulation material disposed between the conducting layers/electrodes. Furthermore, in still another aspect of the present invention, the one or more conducting layers such as the electrodes 401, 402, 403 may be disposed on opposing sides of the substrate 404.

Referring back to the Figures, in one embodiment, the transmitter unit 102 (FIG. 1) is configured to detect the current signal from the sensor 101 (FIG. 1) and the skin temperature near the sensor 101, which are preprocessed by, for example, the transmitter processor 204 (FIG. 2) and transmitted to the receiver unit (for example, the primary receiver unit 104 (FIG. 1)) periodically at a predetermined time interval, such as for example, but not limited to, once per minute, once every two minutes, once every five minutes, or once every ten minutes. Additionally, the transmitter unit 102 may be configured to perform sensor insertion and/or removal detection and data quality analysis, information pertaining to which are also transmitted to the receiver unit 104 periodically at the predetermined time interval. In turn, the receiver unit 104 may be configured to perform, for example, skin temperature compensation as well as calibration of the sensor data received from the transmitter 102.

For example, in one aspect, the transmitter unit 102 may be configured to oversample the sensor signal at a nominal rate of four samples per second, which allows the analyte anti-aliasing filter in the transmitter unit 102 to attenuate noise (for example, due to effects resulting from motion or movement of the sensor after placement) at frequencies above 2 Hz. More specifically, in one embodiment, the transmitter processor 204 may be configured to include a digital filter to reduce aliasing noise when decimating the four Hz sampled sensor data to once per minute samples for transmission to the receiver unit 104. As discussed in further detail below, in one aspect, a two stage Kaiser Finite Impulse Response (FIR) filter may be used to perform the digital filtering for anti-aliasing. While Kaiser FIR filter may be used for digital filtering of the sensor signals, within the scope of the present disclosure, other suitable filters may be used to filter the sensor signals.

In one aspect, the temperature measurement section 203 of the transmitter unit 102 may be configured to measure once per minute the on skin temperature near the analyte sensor at the end of the minute sampling cycle of the sensor signal. Within the scope of the present disclosure, different sample rates may be used which may include, for example, but are not limited to, measuring the on skin temperature for each 30 second periods, each two minute periods, and the like. Additionally, as discussed above, the transmitter unit 102 may be configured to detect sensor insertion, sensor signal settling after sensor insertion, and sensor removal, in addition to detecting for sensor—transmitter system failure modes and sensor signal data integrity. Again, this information is transmitted periodically by the transmitter unit 102 to the receiver unit 104 along with the sampled sensor signals at the predetermined time intervals.

Referring again to the Figures, as the analyte sensor measurements are affected by the temperature of the tissue around the transcutaneously positioned sensor 101, in one aspect, compensation of the temperature variations and affects on the sensor signals are provided for determining the corresponding glucose value. Moreover, the ambient temperature around the sensor 101 may affect the accuracy of the on skin temperature measurement and ultimately the glucose value determined from the sensor signals. Accordingly, in one aspect, a second temperature sensor is provided in the transmitter unit 102 away from the on skin temperature sensor (for example, physically away from the temperature measurement section 203 of the transmitter unit 102), so as to provide compensation or correction of the on skin temperature measurements due to the ambient temperature effects. In this manner, the accuracy of the estimated glucose value corresponding to the sensor signals may be attained.

In one aspect, the processor 204 of the transmitter unit 102 may be configured to include the second temperature sensor, and which is located closer to the ambient thermal source within the transmitter unit 102. In other embodiments, the second temperature sensor may be located at a different location within the transmitter unit 102 housing where the ambient temperature within the housing of the transmitter unit 102 may be accurately determined.

Figure 5:
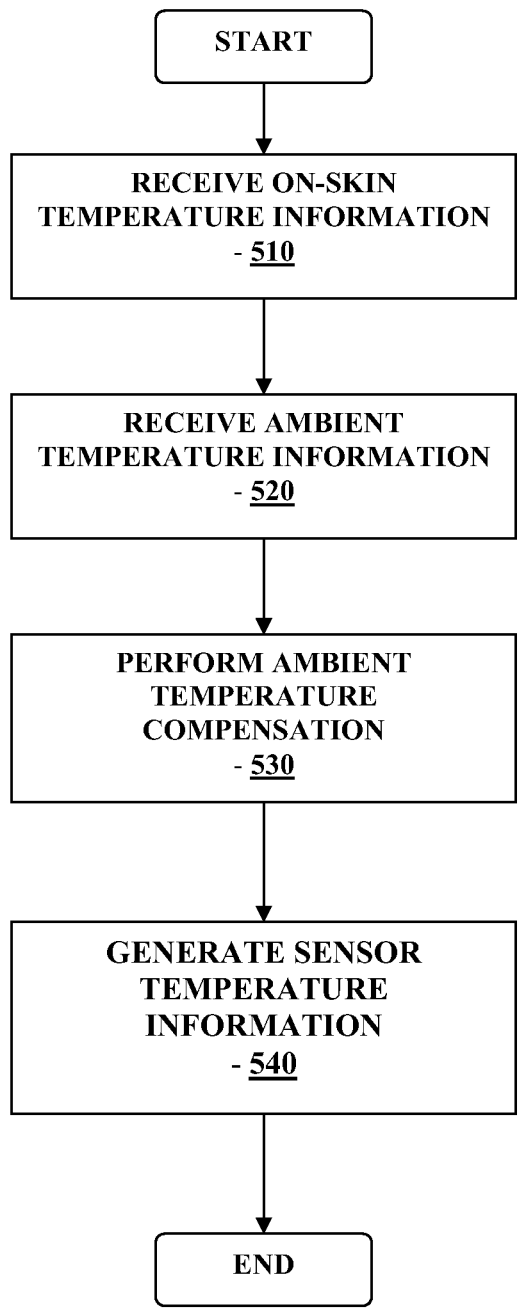
FIG. 5 is a flowchart illustrating ambient temperature compensation routine for determining on-skin temperature information in accordance with one embodiment of the present invention.

Referring now to FIG. 5, in one aspect, is an ambient temperature compensation routine for determining the on-skin temperature level for use in the glucose estimation determination based on the signals received from the sensor 101. Referring to FIG. 5, for each sampled signal from the sensor 101, a corresponding measured temperature information is received (510), for example, by the processor 204 from the temperature measurement section 203 (which may include, for example, a thermistor provided in the transmitter unit 102). In addition, a second temperature measurement is obtained (520), for example, including a determination of the ambient temperature level using a second temperature sensor provided within the housing of the transmitter unit 102.

In one aspect, based on a predetermined ratio of thermal resistances between the temperature measurement section 203 and the second temperature sensor (located, for example, within the processor 204 of the transmitter unit 102), and between the temperature measurement section 203 and the skin layer on which the transmitter unit 102 is placed and coupled to the sensor 101, ambient temperature compensation may be performed (530), to determine the corresponding ambient temperature compensated on skin temperature level (540). In one embodiment, the predetermined ratio of the thermal resistances may be approximately 0.2. However, within the scope of the present invention, this thermal resistance ratio may vary according to the design of the system, for example, based on the size of the transmitter unit 102 housing, the location of the second temperature sensor within the housing of the transmitter unit 102, and the like.

With the ambient temperature compensated on-skin temperature information, the corresponding glucose value from the sampled analyte sensor signal may be determined.

Referring again to FIG. 2, the processor 204 of the transmitter unit 102 may include a digital anti-aliasing filter. Using analog anti-aliasing filters for a one minute measurement data sample rate would require a large capacitor in the transmitter unit 102 design, and which in turn impacts the size of the transmitter unit 102. As such, in one aspect, the sensor signals may be oversampled (for example, at a rate of 4 times per second), and then the data is digitally decimated to derive a one-minute sample rate.

As discussed above, in one aspect, the digital anti-aliasing filter may be used to remove, for example, signal artifacts or otherwise undesirable aliasing effects on the sampled digital signals received from the analog interface 201 of the transmitter unit 102. For example, in one aspect, the digital anti-aliasing filter may be used to accommodate decimation of the sensor data from approximately four Hz samples to one-minute samples. In one aspect, a two stage FIR filter may be used for the digital anti-aliasing filter, and which includes improved response time, pass band and stop band properties.

Figure 6:
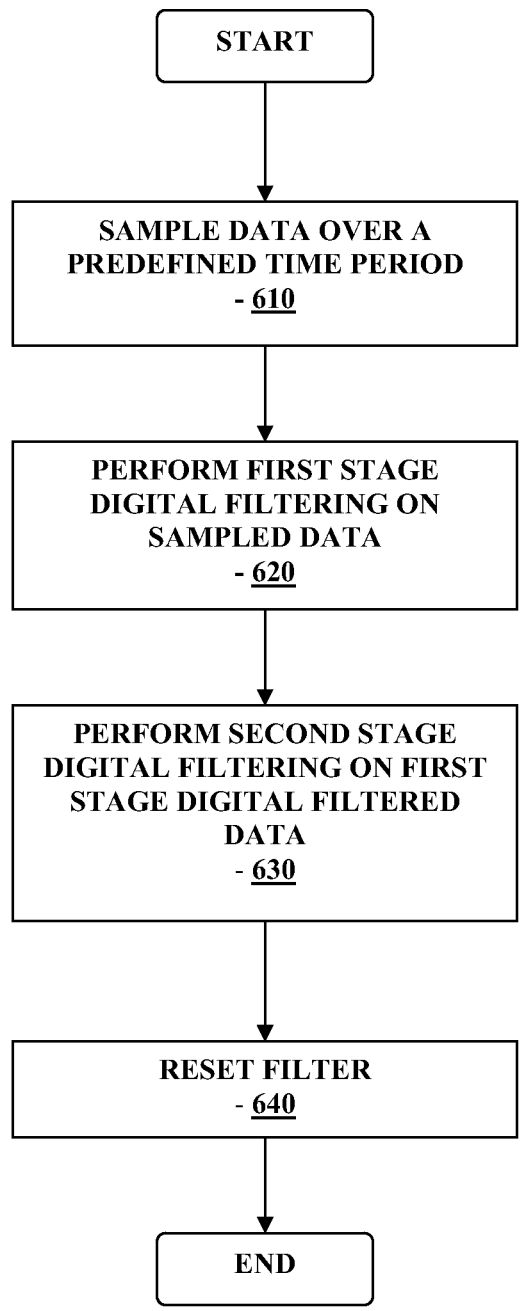
FIG. 6 is a flowchart illustrating digital anti-aliasing filtering routing in accordance with one embodiment of the present invention.

Referring to FIG. 6, a routine for digital anti-aliasing filtering is shown in accordance with one embodiment. As shown, in one embodiment, at each predetermined time period such as every minute, the analog signal from the analog interface 201 corresponding to the monitored analyte level received from the sensor 101 (FIG. 1) is sampled (610). For example, at every minute, in one embodiment, the signal from the analog interface 201 is over-sampled at approximately 4 Hz. Thereafter, the first stage digital filtering on the over-sampled data is performed (620), where, for example, a 1/6 down-sampling from 246 samples to 41 samples is performed, and the resulting 41 samples is further down-sampled at the second stage digital filtering (630) such that, for example, a 1/41 down-sampling is performed from 41 samples (from the first stage digital filtering), to a single sample. Thereafter, the filter is reset (640), and the routine returns to the beginning for the next minute signal received from the analog interface 201.

While the use of FIR filter, and in particular the use of Kaiser FIR filter, is within the scope of the present invention, other suitable filters, such as FIR filters with different weighting schemes or Infinite Impulse Response (IIR) filters, may be used.

Referring yet again to the Figures, the transmitter unit 102 may be configured in one embodiment to periodically perform data quality checks including error condition verifications and potential error condition detections, and also to transmit the relevant information related to one or more data quality, error condition or potential error condition detection to the receiver unit 104 with the transmission of the monitored sensor data. For example, in one aspect, a state machine may be used in conjunction with the transmitter unit 102 and which may be configured to be updated four times per second, the results of which are transmitted to the receiver unit 104 every minute.

In particular, using the state machine, the transmitter unit 102 may be configured to detect one or more states that may indicate when a sensor is inserted, when a sensor is removed from the user, and further, may additionally be configured to perform related data quality checks so as to determine when a new sensor has been inserted or transcutaneously positioned under the skin layer of the user and has settled in the inserted state such that the data transmitted from the transmitter unit 102 does not compromise the integrity of signal processing performed by the receiver unit 104 due to, for example, signal transients resulting from the sensor insertion.

That is, when the transmitter unit 102 detects low or no signal from the sensor 101, which is followed by detected signals from the sensor 101 that is above a given signal, the processor 204 may be configured to identify such transition as monitored signal levels and associate with a potential sensor insertion state. Alternatively, the transmitter unit 102 may be configured to detect the signal level above the other predetermined threshold level, which is followed by the detection of the signal level from the sensor 101 that falls below the same or another predetermined threshold level. In such a case, the processor 204 may be configured to associate or identify such transition or condition in the monitored signal levels as a potential sensor removal state.

Accordingly, when either of potential sensor insertion state or potential sensor removal state, or any other state, is detected by the transmitter unit 102, this information is transmitted to the receiver unit 104, and in turn, the receiver unit may be configured to prompt the user for confirmation of either of the detected potential sensor related state. In one aspect, the current state information is continuously or intermittently transmitted to the receiver unit for example, where when there is a failed transmission (for example, a missed data packet from the transmitter to the receiver unit), the current state information is known by the receiver so as to determine the state transition. In another aspect, the sensor insertion state or potential sensor removal state may be detected or determined by the receiver unit based on one or more signals received from the transmitter unit 102.

For example, in one aspect, the transmitter unit may be coupled to one or more sensors, each sensor configured to generate one or more signals associated with the analyte being monitored. Alternatively, the receiver unit may be coupled, wirelessly or otherwise, to one or more transmitters, each with their own sensor signal. In another aspect, the sensor/transmitter configuration may include a mechanism to detect connection between the sensor/transmitter, and/or sensor implantation in the patient's tissue. For instance, a conductivity loop may be incorporated into the sensor/transmitter configuration, such that an electrically conductive path is provided along the sensor length with an opening at the portion of the sensor that is located in the patient's analyte being monitored, and a return path provided along the sensor length, with two contacts formed to meet with two contacts on the transmitter. The transmitter may be configured to apply electrical current to the contacts and detect current flow when a) both contacts are in electrical contact with the sensor contacts, and b) the sensor is positioned properly in the analyte being monitored, closing the electrical circuit with a finite resistance that allows detectable current to flow.

The transmitter and/or receiver unit may be designed to use this detected signal alone or in combination with the sensor signal to determine the operational state of the sensor. In another aspect, the conductive path may be provided so that it indicates the contact between the sensor and the transmitter, and not configured to pass along the length of the sensor. Again, the transmitter and/or receiver may be configured to use this signal alone or in combination with the sensor signal to determine the operational state of the sensor. In yet another embodiment, a magnetic detection mechanism may be provided to detect sensor/transmitter connection where the transmitter unit may be configured to electromagnetically detect a magnet located in the sensor when in close proximately thereto.

In another aspect, the sensor insertion state or potential sensor removal state may be detected or determined by the receiver unit based on one or more signals from the transmitter unit 102 and one or more signals derived at the receiver unit 104. For example, similar to an alarm condition or a notification to the user, the receiver unit 104 may be configured to display a request or a prompt on the display or an output unit of the receiver unit 104 a text and/or other suitable notification message to inform the user to confirm the state of the sensor 101.

For example, the receiver unit 104 may be configured to display the following message: "New Sensor Inserted" or "Did you insert a new Sensor??" or a similar notification in the case where the receiver unit 104 receives one or more signals from the transmitter unit 102 associated with the detection of the signal level below the predetermined threshold level for the predefined period of time, followed by the detection of the signal level from the sensor 101 above another predetermined threshold level for another predefined period of time. Alternatively, the receiver unit may display this message when it receives the "new sensor" or "sensor inserted" operational state data from the transmitter, that has changed from the previous operational state data, stored in the receiver unit, indicating "sensor removed". Indeed, in one aspect, the receiver unit may be configured to maintain a state machine, and if it is in the "sensor removed" state, the receiver is configured to look for "new sensor" or "sensor stable" transitions to determine if it needs to change state.

Additionally, the receiver unit 104 may be configured to display the following message: "Sensor removed" or "Did you remove the sensor?" or a similar notification in the case where the receiver unit 104 received one or more signals from the transmitter unit 102 associated with the detection of the signal level from the sensor 101 that is above the other predetermined threshold level for the other predefined period of time, which is followed by the detection of the signal level from the sensor 101 that falls below the predetermined threshold level for the predefined period of time. Again, in another embodiment, the receiver unit may display this message when it receives the "sensor removed" operational state data from the transmitter, that has changed from the previous operational state data, stored in the receiver unit, indicating "new sensor" or "sensor inserted".

Based on the user confirmation received, the receiver unit 104 may be further configured to execute or perform additional related processing and routines in response to the user confirmation or acknowledgement. For example, when the user confirms, using the user interface input/output mechanism of the receiver unit 104, for example, that a new sensor has been inserted, the receiver unit 104 may be configured to initiate new sensor insertion related routines including, such as, for example, a sensor calibration routine including, for example, calibration timer, sensor expiration timer and the like. Alternatively, when the user confirms or it is determined that the sensor 101 is not properly positioned or otherwise removed from the insertion site, the receiver unit 104 may be accordingly configured to perform related functions such as, for example, stop displaying of the glucose values/levels, or deactivating the alarm monitoring conditions.

On the other hand, in response to the potential sensor insertion notification generated by the receiver unit 104, if the user confirms that no new sensor has been inserted, then the receiver unit 104 in one embodiment is configured to assume that the sensor 101 is in acceptable operational state, and continues to receive and process signals from the transmitter unit 102.

In this manner, in cases, for example, when there is momentary movement or temporary dislodging of the sensor 101 from the initially positioned transcutaneous state, or when one or more of the contact points between sensor 101 and the transmitter unit 102 are temporarily disconnected, but otherwise, the sensor 101 is operational and within its useful life, the routine above provides an option to the user to maintain the usage of the sensor 101, to not replace the sensor 101 prior to the expiration of its useful life. In this manner, in one aspect, false positive indications of sensor 101 failure may be identified and addressed.

Figure 7:
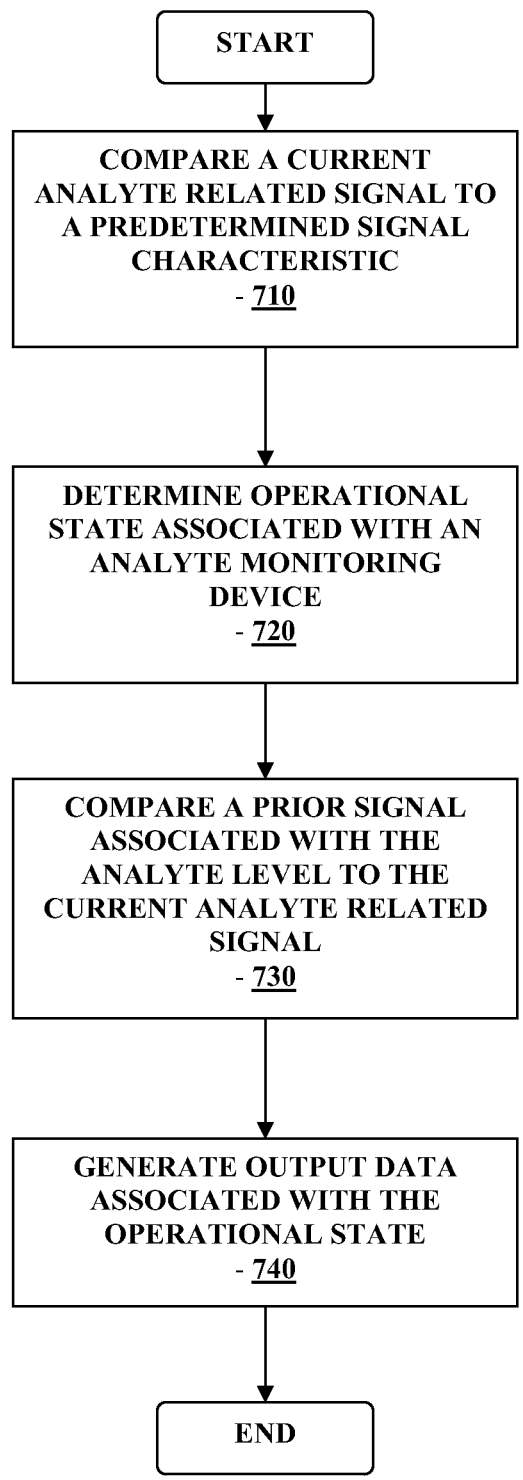
FIG. 7 is a flowchart illustrating actual or potential sensor insertion or removal detection routine in accordance with one embodiment of the present invention.

For example, FIG. 7 is a flowchart illustrating an actual or potential sensor insertion or removal detection routine in accordance with one embodiment of the present invention. Referring to the Figure, the state machine is in an initial operational state, for instance, the "sensor removed" state. Next, the current analyte related signal is received and then compared to one or more predetermined signal characteristics. One predetermined signal characteristic, associated with new sensor insertion, is for the signal level to exceed 18 ADC (analog to digital conversion) counts continuously for approximately 10 seconds. Another predetermined signal characteristic, associated with signal settling (that is, the signal transient associated with sensor insertion has subsided), is for the signal level to exceed 9 ADC counts and the result of the current signal minus a previous signal from 10 seconds prior, retrieved from storage, must be less than 59 ADC counts, both continuously for a duration of 90 seconds.

Another predetermined signal characteristic, associated with sensor removal, is for the signal level to be less than 9 ADC counts continuously for 10 seconds. It is to be noted that other values for levels and durations may be contemplated to be more suitable for various designs and are within the scope of the present disclosure. Also, in particular embodiments, the signal characteristic criteria may allow one or more violations of the signal threshold or rate deviances (such as exceeding the threshold or rate). Also, the duration may be variable, where that duration and threshold is determined by some other characteristic, such as present operational state. Other variations in signal characteristics may be contemplated based on the detectability of other contemplated operational states or on the previously discussed operational states. Also, prefiltering of the signals may be included prior to the comparison with predetermined signal characteristics, as appropriate.

Referring back to the Figure, a new operational state is determined. In one aspect this is based on the present operational state, and the results from the signal being compared with predetermined signal characteristics. For example, if the present operational state is "sensor removed", and the result of the predetermined signal characteristic comparison associated with new sensor insertion is true, then the operational state will transition to the "new sensor" state. Likewise, if the present operational state is "sensor inserted" or "new sensor", and the result of the predetermined signal characteristic comparison associated with sensor removal is true, then the operational state will transition to the "sensor removed" state. If the comparison results are false, then the operational state stays unchanged. Similarly, other state transition operations can be contemplated and implemented as required.

In yet another aspect, based on the present operational state, only predetermined signal characteristics relevant to that operational state may be compared with the signal. Also, data quality status, as determined upon every received new signal, may alter the state transition operation. For instance, state transitions may be precluded if it is determined that data quality is invalid, and not allowed until data quality is determined to be valid.

In this manner, in one aspect of the present invention, based on a transition state of the received analyte related signals, it may be possible to determine the state of the analyte sensor and, based on which, the user or the patient to confirm, whether the analyte sensor is in the desired or proper position, has been temporarily dislocated, or otherwise removed from the desired insertion site so as to require a new analyte sensor.

In this manner, in one aspect, when the monitored signal from the sensor 101 crosses a transition level (for example, from no or low signal level to a high signal level, or vice versa), the transmitter unit 102 may be configured to generate an appropriate output data associated with the sensor signal transition, for transmission to the receiver unit 104 (FIG. 1). Additionally, as discussed in further detail below, in another embodiment, the determination of whether the sensor 101 has crossed a transition level may be determined by the receiver/monitor unit 104/106 based, at least in part, on the one or more signals received from the transmitter unit 102.

Figure 8:
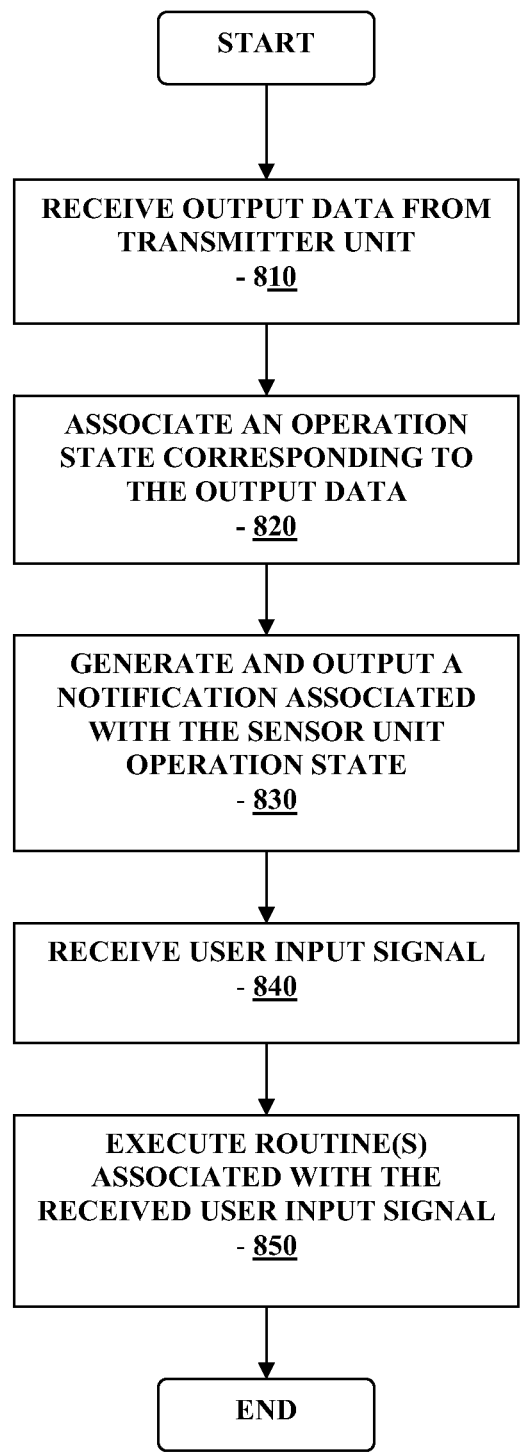
FIG. 8 is a flowchart illustrating receiver unit processing corresponding to the actual or potential sensor insertion or removal detection routine of FIG. 7 in accordance with one embodiment of the present invention.

FIG. 8 is a flowchart illustrating receiver unit processing corresponding to the actual or potential sensor insertion or removal detection routine of FIG. 7 in accordance with one embodiment of the present invention. Referring now to FIG. 8, when the receiver unit 104 receives the generated output data from the transmitter unit 102 (810), it is related to a corresponding operation state such as a potential new operational state of the sensor 101 (820). Moreover, if the potential new operational state is different than the current operational state, a notification associated with the sensor operation state is generated and output to the user on the display unit or any other suitable output segment of the receiver unit 104 (830). When a user input signal is received in response to the notification associated with the sensor state operation state (840), the receiver unit 104 is configured to execute one or more routines associated with the received user input signal (850).

That is, as discussed above, in one aspect, if the user confirms that the sensor 101 has been removed, the receiver unit 104 may be configured to terminate or deactivate alarm monitoring and glucose displaying functions. On the other hand, if the user confirms that a new sensor 101 has been positioned or inserted into the user, then the receiver unit 104 may be configured to initiate or execute routines associated with the new sensor insertion, such as, for example, calibration procedures, establishing calibration timer, and establishing sensor expiration timer.

In a further embodiment, based on the detected or monitored signal transition, the receiver/monitor unit may be configured to determine the corresponding sensor state without relying upon the user input or confirmation signal associated with whether the sensor is dislocated or removed from the insertion site, or otherwise, operating properly.

Figure 9:
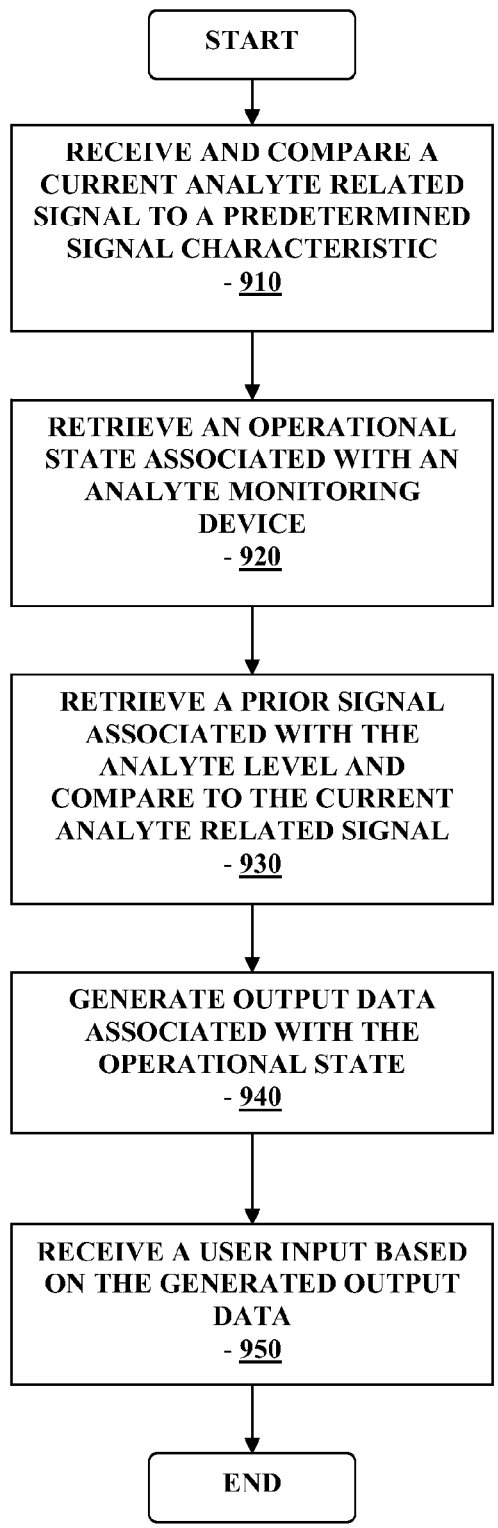
FIG. 9 is a flowchart illustrating data processing corresponding to the actual or potential sensor insertion or removal detection routine in accordance with another embodiment of the present invention.

FIG. 9 is a flowchart illustrating data processing corresponding to the actual or potential sensor insertion or removal detection routine in accordance with another embodiment of the present invention. Referring to FIG. 9, a current analyte related signal is received from the transmitter unit and compared to a predetermined signal characteristic (910). Thereafter, a new potential operational state associated with an analyte monitoring device such as, for example, the sensor 101 (FIG. 1) is retrieved (920) from a storage unit or otherwise resident in, for example, a memory of the receiver/monitor unit. Additionally, a prior analyte related signal is also retrieved from the storage unit, and compared to the current analyte related signal received (930). An output data is generated which is associated with the operational state, and which, at least in part, is based on the one or more of the received current analyte related signal and the retrieved prior analyte related signal.

Referring again to FIG. 9, when the new potential operational state is generated, a corresponding user input command or signal is received (950) in response to the generated output data (940), which may include one or more of a confirmation, verification, or rejection of the operational state related to the analyte monitoring device.

Figure 10:
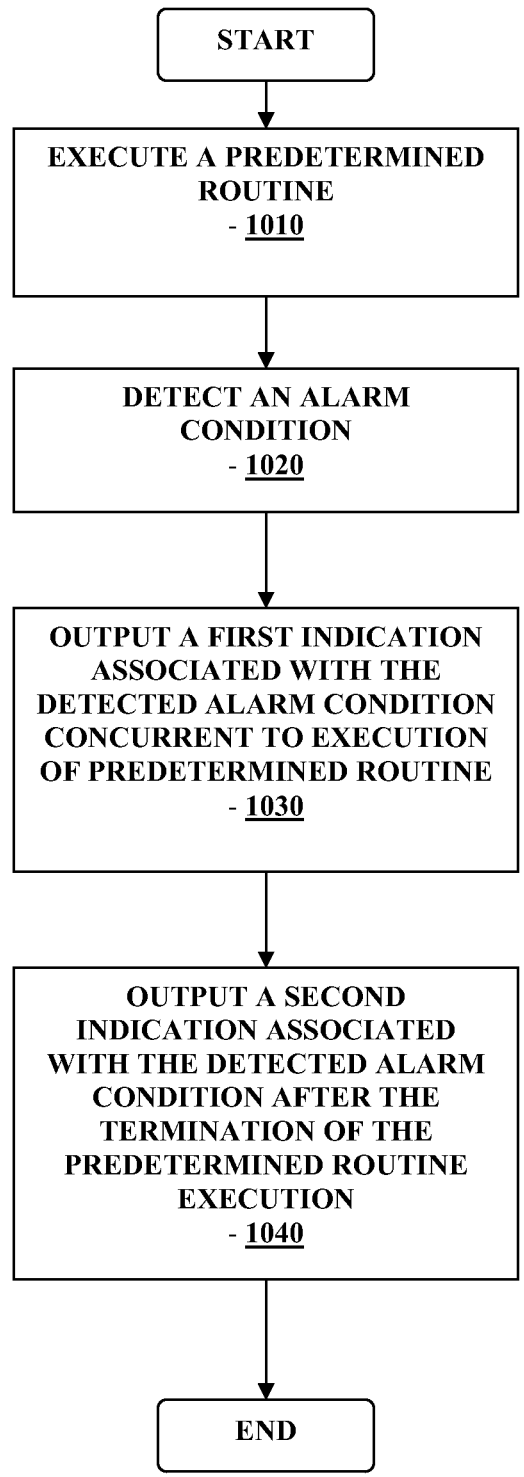
FIG. 10 is a flowchart illustrating a concurrent passive notification routine in the data receiver/monitor unit of the data monitoring and management system of FIG. 1 in accordance with one embodiment of the present invention.

FIG. 10 is a flowchart illustrating a concurrent passive notification routine in the data receiver/monitor unit of the data monitoring and management system of FIG. 1 in accordance with one embodiment of the present invention. Referring to FIG. 10, a predetermined routine is executed (1010). During the execution of the predetermined routine, an alarm condition is detected (1020), and when the alarm or alert condition is detected, a first indication associated with the detected alarm or alert condition is output concurrent to the execution of the predetermined routine (1030).

That is, in one embodiment, when a predefined routine is being executed, and an alarm or alert condition is detected, a notification is provided to the user or patient associated with the detected alarm or alert condition, but which does not interrupt or otherwise disrupt the execution of the predefined routine. Referring back to FIG. 10, upon termination of the predetermined routine, another output or second indication associated with the detected alarm condition is output or displayed (1040).

More specifically, in one aspect, the user interface notification feature associated with the detected alarm condition is output to the user only upon the completion of an ongoing routine which was in the process of being executed when the alarm condition is detected. As discussed above, when such alarm condition is detected during the execution of a predetermined routine, a temporary alarm notification such as, for example, a backlight indicator, a text output on the user interface display, a reverse-video flashing of text, icon, a newly displayed flashing bar, or any other suitable output indication may be provided to alert the user or the patient of the detected alarm condition substantially in real time, but which does not disrupt an ongoing routine.

Within the scope of the present invention, the ongoing routine or the predetermined routine being executed may include one or more of performing a finger stick blood glucose test (for example, for purposes of periodically calibrating the sensor 101), or any other processes that interface with the user interface, for example, on the receiver/monitor unit 104/106 (FIG. 1) including, but not limited to the configuration of device settings, review of historical data such as glucose data, alarms, events, entries in the data log, visual displays of data including graphs, lists, and plots, data communication management including RF communication administration, data transfer to the data processing terminal 105 (FIG. 1), or viewing one or more alarm conditions with a different priority in a preprogrammed or determined alarm or notification hierarchy structure.

In this manner, in one aspect of the present invention, the detection of one or more alarm conditions may be presented or notified to the user or the patient, without interrupting or disrupting an ongoing routine or process in, for example, the receiver/monitor unit 104/106 of the data monitoring and management system 100 (FIG. 1).

A method in accordance with one embodiment includes detecting a first temperature related signal from a first source, detecting a second temperature related signal from a second source, the second source located at a predetermined distance from the first source, and estimating an analyte temperature related signal based on the first and second detected temperature signals.

The first source in one aspect may be located substantially in close proximity to a transcutaneously positioned analyte sensor, and more specifically, in one embodiment, the first source may be located approximately 0.75 inches from the analyte sensor.

In a further embodiment, the analyte temperature related signal may be estimated based on a predetermined value associated with the detected first and second temperature related signals, where the predetermined value may include a ratio of thermal resistances associated with the first and second sources.

The method in a further aspect may include determining a glucose value based on the estimated analyte temperature related signal and a monitored analyte level. The second temperature related signal in yet another aspect may be related to an ambient temperature source.

An apparatus in a further embodiment may include a housing, an analyte sensor coupled to the housing and transcutaneously positioned under a skin layer of a user, a first temperature detection unit coupled to the housing configured to detect a temperature associated with the analyte sensor, and a second temperature detection unit provided in the housing and configured to detect an ambient temperature.

The one or more of the first temperature detection unit or the second temperature detection unit may include one or more of a thermistor, a semiconductor temperature sensor, or a resistance temperature detector (RTD).

The apparatus in a further aspect may also include a processor, where at least a portion of the second temperature detection unit may be provided within the processor.

In another embodiment, the processor may be configured to receive the temperature associated with the analyte sensor, the ambient temperature, and an analyte related signal from the analyte sensor, and also, the processor may be configured to estimate an analyte temperature related signal based on the temperature associated with the analyte sensor, and the ambient temperature.

Also, the processor may be configured to determine a glucose value based on the estimated analyte temperature related signal and an analyte related signal from the analyte sensor.

In still another aspect, the analyte temperature related signal may be estimated based on a predetermined value associated with the detected temperature associated with the analyte sensor, and the ambient temperature, where the predetermined value may include a ratio of thermal resistances associated with the temperature associated with the analyte sensor, and the ambient temperature.

Alternatively, the predetermined value in still another aspect may be variable based on an error feedback signal associated with the monitored analyte level by the analyte sensor, where the error feedback signal may be associated with a difference between a blood glucose reference value and the analyte sensor signal.

The apparatus may also include a transmitter unit configured to transmit one or more signals associated with the detected temperature associated with the analyte sensor, detected ambient temperature, an analyte related signal from the analyte sensor, analyte temperature related signal based on the temperature associated with the analyte sensor, and the ambient temperature, or a glucose value based on the estimated analyte temperature related signal and the analyte related signal from the analyte sensor.

The transmitter unit may include an RF transmitter.

A system in accordance with still another embodiment may include a data receiver configured to receive a first temperature related signal from a first source, a second temperature related signal from a second source, the second source located at a predetermined distance from the first source, and a processor operatively coupled to the data receiver, and configured to estimate an analyte temperature related signal based on the first and second detected temperature signals.

An apparatus in accordance with a further embodiment includes a digital filter unit including a first filter stage and a second filter stage, the digital filter unit configured to receive a sampled signal, where the first filter stage is configured to filter the sampled signal based on a first predetermined filter characteristic to generate a first filter stage output signal, and further, where the second filter stage is configured to filter the first filter stage output signal based on a second predetermined filter characteristic to generate an output signal associated with a monitored analyte level.

The sampled signal may include an over-sampled signal at a frequency of approximately 4 Hz.

The digital filter unit may include one of a Finite Impulse Response (FIR) filter, or an Infinite Impulse Response (IIR) filter.

The first and the second filter stages may include respective first and second down sampling filter characteristics.

Also, the one or more of the first and second filter stages may include down sampling the sampled signal or the first filter stage output signal, respectively, where the received sampled signal may be associated with the monitored analyte level of a user.

In another aspect, the digital filter unit may be configured to receive the sampled signal at a predetermined time interval.

The predetermined time interval in one aspect may include one of approximately 30 seconds, approximately one minute, approximately two minutes, approximately five minutes, or any other suitable time periods.

A method in accordance with yet another embodiment includes receiving a sampled signal associated with a monitored analyte level of a user, performing a first stage filtering based on the received sampled signal to generate a first stage filtered signal, performing a second stage filtering based on the generated first stage filtered signal, and generating a filtered sampled signal.

The sampled signal may include an over-sampled signal at a frequency of approximately 4 Hz, and also, where the first and the second stage filtering may include a respective first and second down sampling based on one or more filter characteristics.

The received sampled signal in one aspect may be periodically received at a predetermined time interval, where the predetermined time interval may include one of approximately 30 seconds, approximately one minute, approximately two minutes, or approximately five minutes.

A method in still another embodiment may include receiving a signal associated with an analyte level of a user, determining whether the received signal deviates from a predetermined signal characteristic, determining an operational state associated with an analyte monitoring device, comparing a prior signal associated with the analyte level of the user to the received signal, generating an output data associated with the operational state of the analyte monitoring device based on one or more of the received signal and the prior signal.

The predetermined signal characteristic in one embodiment may include a signal level transition from below a first predetermined level to above the first predetermined level, a signal level transition from above a second predetermined level to below the second predetermined threshold, a transition from below a predetermined signal rate of change threshold to above the predetermined signal rate of change threshold, or a transition from above the predetermined signal rate of change threshold to below the predetermined signal rate of change threshold.

In one aspect, the first predetermined level and the second predetermined level each may include one of approximately 9 ADC counts or approximately 18 ADC counts, or any other suitable signal levels or analog to digital converter (ADC) counts that respectively represent or correspond to a no sensor signal state, a sensor signal state, or the like.

The predetermined signal characteristic may include in one aspect, a transition from below a predetermined level to above and wherein the signal is maintained above the predetermined level for a predetermined period of time, where the predetermined period of time may include one of approximately 10 seconds, 30 seconds, or less than 30 seconds, or greater than 30 seconds, or any other suitable time periods.

In a further aspect, the operational state may include a no detected sensor state, or a sensor presence state.

The output data in one embodiment may include a user notification alert.

Further, the output data may include an indicator to start one or more processing timers associated with a respective one or more data processing routines, where the one or more processing timers may include a respective one of a calibration timer, or a sensor expiration timer.

The method may include receiving a user input data based on the output data, where the user input data may include a user confirmation of one of the change in operational state or no change in operational state.

The method may further include modifying the operational state, where the operational state may be modified based on one of the received user input data, or based on the generated output data.

The method may include presenting the output data, where presenting the output data may include one or more of visually presenting the output data, audibly presenting the output data, vibratorily presenting the output data, or one or more combinations thereof.

The analyte level may include glucose level of the user.

The operational state may include one of an analyte sensor removal state, an analyte sensor insertion state, an analyte sensor dislocation state, an analyte sensor insertion with an associated transient signal state, or an analyte sensor insertion with an associated stabilized signal state.

An apparatus in still yet another embodiment may include a data processing unit including a data processor configured to determine whether a received signal associated with an analyte level of a user deviates from a predetermined signal characteristic, determine an operational state associated with an analyte monitoring device, compare a prior signal associated with the analyte level of the user to the received signal, and generate an output data associated with the operational state of the analyte monitoring device based on one or more of the received signal or the prior signal.

The data processing unit may include a communication unit operatively coupled to the data processor and configured to communicate one or more of the received signal, the prior signal, and the output data associated the operational state of the analyte monitoring device.

The communication unit may include one of an RF transmitter, an RF receiver, an infrared data communication device, a Bluetooth® data communication device, or a Zigbee® data communication device.

The data processing unit may include a storage unit operatively coupled to the data processor to store one or more of the received signal associated with the analyte level, the predetermined signal characteristic, the operational state associated with the analyte monitoring device, the prior signal associated with the analyte level of the user, or the output data associated with the operational state of the analyte monitoring device.

A method in accordance with still yet a further embodiment may include receiving a signal associated with an analyte level of a user, determining whether the received signal deviates from a predetermined signal characteristic, determining an operational state associated with an analyte monitoring device, comparing a prior signal associated with the analyte level of the user to the received signal, presenting an output data associated with the operational state of the analyte monitoring device based, at least in part, on one or more of the received signal or the prior signal, and receiving a user input data based on the presented output data.

In still another aspect, the predetermined signal characteristic may include a signal level transition from below a first predetermined level to above the first predetermined level, a signal level transition from above a second predetermined level to below the second predetermined level, a transition from below a predetermined signal rate of change threshold to above the predetermined signal rate of change threshold, and a transition from above the predetermined signal rate of change threshold to below the predetermined signal rate of change threshold, and further, where the first predetermined level and the second predetermined level each may include one of approximately 9 ADC counts or approximately 18 ADC counts, or other predetermined ADC counts or signal levels.

The predetermined signal characteristic in another aspect may include a transition from below a predetermined level to above and wherein the signal is maintained above the predetermined level for a predetermined period of time which may include, for example, but is not limited to, approximately 10 seconds, 30 seconds, or less than 30 seconds, or greater than 30 seconds.

Further, the operational state may include a no detected sensor state, or a sensor presence state.

Moreover, the output data may include a user notification alert.

The output data may include an indicator to start one or more processing timers associated with a respective one or more data processing routines, where the one or more processing timers may include a respective one of a calibration timer, or a sensor expiration timer.

In another aspect, the user input data may include a user confirmation of one of the change in operational state or no change in operational state.

The method may include modifying the operational state based on, for example, one of the received user input data, or based on the generated output data.

Additionally, presenting the output data may include one or more of visually presenting the output data, audibly presenting the output data, vibratorily presenting the output data, or one or more combinations thereof.

Also, the operational state may include one of an analyte sensor removal state, an analyte sensor insertion state, an analyte sensor dislocation state, an analyte sensor insertion with an associated transient signal state, or an analyte sensor insertion with an associated stabilized signal state.

A data processing device in accordance with one embodiment may include a user interface unit, and a data processor operatively coupled to the user interface unit, the data processor configured to receive a signal associated with an analyte level of a user, determine whether the received signal deviates from a predetermined signal characteristic, determine an operational state associated with an analyte monitoring device, compare a prior signal associated with the analyte level of the user to the received signal, present in the user interface unit an output data associated with the operational state of the analyte monitoring device based, at least in part, on one or more of the received signal or the prior signal, and to receive a user input data from the user interface unit based on the presented output data.

The user interface unit in one aspect may include one or more of a user input unit, a visual display unit, an audible output unit, a vibratory output unit, or a touch sensitive user input unit.

In one embodiment, the device may include a communication unit operatively coupled to the data processor and configured to communicate one or more of the received signal, the prior signal, and the output data associated with the operational state of the analyte monitoring device, where the communication unit may include, for example, but is not limited to, one of an RF transmitter, an RF receiver, an infrared data communication device, a Bluetooth® data communication device, a Zigbee® data communication device, or a wired connection.

The data processing device may include a storage unit operatively coupled to the data processor to store one or more of the received signal associated with the analyte level, the predetermined signal characteristic, the operational state associated with the analyte monitoring device, the prior signal associated with the analyte level of the user, or the output data associated with the operational state of the analyte monitoring device.

A method in accordance with still yet another embodiment may include executing a predetermined routine associated with an operation of an analyte monitoring device, detecting one or more predefined alarm conditions associated with the analyte monitoring device, outputting a first indication associated with the detected one or more predefined alarm conditions during the execution of the predetermined routine, outputting a second indication associated with the detected one or more predefined alarm conditions after the execution of the predetermined routine, where the predetermined routine is executed without interruption during the outputting of the first indication.

In one aspect, the predetermined routine may include one or more processes associated with performing a blood glucose assay, one or more configuration settings, analyte related data review or analysis, data communication routine, calibration routine, or reviewing a higher priority alarm condition notification compared to the predetermined routine, or any other process or routine that requires the user interface.

Moreover, in one aspect, the first indication may include one or more of visual, audible, or vibratory indicators.

Further, the second indication may include one or more of visual, audible, or vibratory indicators.

In one aspect, the first indication may include a temporary indicator, and further, and the second indication may include a predetermined alarm associated with a detected predefined alarm condition.

In still another aspect, the first indication may be active during the execution of the predetermined routine, and may be inactive at the end of the predetermined routine.

Further, the second indication in a further aspect may be active at the end of the predetermined routine.

Moreover, each of the first indication and the second indication may include one or more of a visual text notification alert, a backlight indicator, a graphical notification, an audible notification, or a vibratory notification.

The predetermined routine may be executed to completion without interruption.

An apparatus in accordance with still another embodiment may include a user interface, and a data processing unit operatively coupled to the user interface, the data processing unit configured to execute a predetermined routine associated with an operation of an analyte monitoring device, detect one or more predefined alarm conditions associated with the analyte monitoring device, output on the user interface a first indication associated with the detected one or more predefined alarm conditions during the execution of the predetermined routine, and output on the user interface a second indication associated with the detected one or more predefined alarm conditions after the execution of the predetermined routine, wherein the predetermined routine is executed without interruption during the outputting of the first indication.

The predetermined routine may include one or more processes associated with performing a blood glucose assay, one or more configuration settings, analyte related data review or analysis, data communication routine, calibration routine, or reviewing a higher priority alarm condition notification compared to the predetermined routine.

The first indication or the second indication or both, in one aspect may include one or more of visual, audible, or vibratory indicators output on the user interface.

In addition, the first indication may include a temporary indicator, and further, wherein the second indication includes a predetermined alarm associated with the detected predefined alarm condition.

Also, the first indication may be output on the user interface during the execution of the predetermined routine, and is not output on the user interface at or prior to the end of the predetermined routine.

Additionally, the second indication may be active at the end of the predetermined routine.

In another aspect, each of the first indication and the second indication may include a respective one or more of a visual text notification alert, a backlight indicator, a graphical notification, an audible notification, or a vibratory notification, configured to output on the user interface.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A method, comprising:
   generating with an analyte sensor a plurality of signals, wherein the plurality of signals have a signal characteristic independent of a measured analyte level of a user;
   determining, using an analyte monitoring device electrically coupled to the analyte sensor and in signal communication with the analyte sensor, whether the signal characteristic of the plurality of generated signals deviates from a predetermined signal characteristic corresponding to signal characteristics of a predetermined operational state of the analyte monitoring device, wherein the predetermined operational state corresponds to an individual one of a plurality of operational states of the analyte monitoring device, wherein each of the plurality of operational states have a corresponding signal characteristic, wherein the plurality of operational states includes an analyte sensor removal state and an analyte sensor insertion state;
   setting a present operational state of the analyte monitoring device based on the signal characteristic of the plurality of generated signals, wherein if the signal characteristic of the plurality of generated signals deviate from the predetermined signal characteristic corresponding to the predetermined operational state the present operational state will differ from the predetermined operational state;
   presenting an output data associated with an operational state of the analyte monitoring device and based at least in part on an analysis of one or more of the plurality of generated signals relative to a prior generated signal; and
   determining a new operational state of the analyte monitoring device based upon user input in response to the output data.

2. The method of claim 1, wherein the predetermined signal characteristic further includes one or more of a signal level transition from below a first predetermined level to above the first predetermined level, a signal level transition from above a second predetermined level to below the second predetermined level, a transition from below a predetermined signal rate of change threshold to above the predetermined signal rate of change threshold, or a transition from above the predetermined signal rate of change threshold to below the predetermined signal rate of change threshold.

3. The method of claim 2, wherein the first predetermined level and the second predetermined level each includes one of approximately 9 ADC counts or approximately 18 ADC counts.

4. The method of claim 1, wherein the predetermined signal characteristic includes a transition from below a predetermined level to above and wherein the signal is maintained above the predetermined level for a predetermined period of time.

5. The method of claim 4, wherein the predetermined period of time includes one of approximately 10 seconds, 30 seconds, less than 30 seconds, or greater than 30 seconds.

6. The method of claim 1, wherein the output data includes a user notification alert.

7. The method of claim 1, wherein the output data includes an indicator to start one or more processing timers associated with a respective one or more data processing routines.

8. The method of claim 7, wherein the one or more processing timers includes a respective one of a calibration timer, or a sensor expiration timer.

9. The method of claim 1, wherein the user input data includes a user confirmation of a transition to the new operational state.

10. The method of claim 1, including transitioning from the present operational state to the new operational state.

11. The method of claim 10, wherein the transitioning from the present operational state to the new operational state is based on the received user input data, or based on the generated output data.

12. The method of claim 1, wherein presenting the output data includes one or more of visually presenting the output data, audibly presenting the output data, vibratorily presenting the output data, or one or more combinations thereof.

13. The method of claim 1, wherein the analyte level includes glucose level of a user.

14. The method of claim 1, wherein the new operational state includes one of an analyte sensor removal state, an analyte sensor insertion state, an analyte sensor dislocation state, an analyte sensor insertion with an associated transient signal state, or an analyte sensor insertion with an associated stabilized signal state.

15. A data processing device, comprising:
    a storage unit;
    a user interface unit; and
    a data processor operatively coupled to the user interface unit and the storage unit, the data processor configured to:
    receive a plurality of signals generated by an analyte sensor, wherein the plurality of signals have a signal characteristic independent of a measured analyte level of a user, the analyte sensor in signal communication with the data processor;
    determine whether the signal characteristic of the plurality of generated signals deviates from a predetermined signal characteristic corresponding to signal characteristics of a predetermined operational state of the analyte monitoring device, wherein the predetermined operational state of the analyte monitoring device corresponds to an individual one of a plurality of operational states of the analyte monitoring device, wherein each of the plurality of operational states have a corresponding signal characteristic, wherein the plurality of operational states includes an analyte sensor removal state and an analyte sensor insertion state;
    set a present operational state of the analyte monitoring device based on the signal characteristic of the plurality of generated signals, wherein if the signal characteristic of the plurality of generated signals deviate from the predetermined signal characteristic corresponding to the predetermined operational state the present operational state will differ from the predetermined operational state;

present in the user interface unit an output data associated with an operational state of the analyte monitoring device and based at least in part on an analysis of one or more of the plurality of generated signals relative to a prior generated signal; and determine a new operational state associated with an analyte monitoring device based upon user input in response to the output data.

16. The device of claim 15, wherein the user interface unit includes one or more of a user input unit, a visual display unit, an audible output unit, a vibratory output unit, or a touch sensitive user input unit.

17. The device of claim 16, including a communication unit operatively coupled to the data processor and configured to communicate one or more of the received signal, the prior signal, and the output data.

18. The device of claim 17, wherein the communication unit includes one of an RF transmitter, an RF receiver, an infrared data communication device, or a short-range data communication device.

19. The device of claim 16, including a storage unit operatively coupled to the data processor to store one or more of the received signal associated with the analyte level, the predetermined signal characteristic, the prior signal, the output data, and the new operational state associated with the analyte monitoring device.

20. The method of claim 1, including transitioning from the present operational state to the new operational state associated with the analyte monitoring device, and executing one or more routines associated with the new operational state.

21. The device of claim 15, wherein the data processor is further configured to transition from the present operational state to the new operational state associated with the analyte monitoring device, and execute one or more routines associated with the new operational state.

22. The method of claim 4, wherein the predetermined time period is 90 seconds or less.

23. The method of claim 1, wherein the predetermined signal characteristic comprises a predetermined analog to digital conversion (ADC) count, wherein the predetermined ADC count includes 9 ADC counts over a predetermined time period.

24. The device of claim 15, wherein the predetermined signal characteristic includes a transition from below a predetermined level to above and wherein the signal is maintained above the predetermined level for a predetermined period of time, wherein the predetermined time period is 90 seconds or less.

25. The device of claim 15, wherein the predetermined signal characteristic comprises a predetermined analog to digital conversion (ADC) count, wherein the predetermined ADC count includes 9 ADC counts over a predetermined time period.

26. The method of claim 1, wherein the plurality of operational states further includes a new analyte sensor insertion state.

27. The device of claim 15, wherein the plurality of operational states further includes a new analyte sensor insertion state.

* * * * *